US010683359B2

(12) United States Patent
Schreiber et al.

(10) Patent No.: US 10,683,359 B2
(45) Date of Patent: *Jun. 16, 2020

(54) ANTI-TNFRSF25 ANTIBODIES

(71) Applicant: Pelican Therapeutics, Inc., Durham, NC (US)

(72) Inventors: Taylor H. Schreiber, Durham, NC (US); Jeff T. Hutchins, Claremore, OK (US)

(73) Assignee: Pelican Therapeutics, Inc., Durham, NC (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/964,775

(22) Filed: Apr. 27, 2018

(65) Prior Publication Data

US 2018/0312599 A1   Nov. 1, 2018

Related U.S. Application Data

(63) Continuation of application No. 15/618,993, filed on Jun. 9, 2017, now Pat. No. 10,005,843.

(60) Provisional application No. 62/348,009, filed on Jun. 9, 2016.

(51) Int. Cl.
| | |
|---|---|
| *C07K 16/28* | (2006.01) |
| *A61K 35/17* | (2015.01) |
| *A61K 39/395* | (2006.01) |
| *A61K 45/06* | (2006.01) |

(52) U.S. Cl.
CPC .......... *C07K 16/2878* (2013.01); *A61K 35/17* (2013.01); *A61K 39/3955* (2013.01); *A61K 45/06* (2013.01); *C07K 2317/24* (2013.01); *C07K 2317/34* (2013.01); *C07K 2317/52* (2013.01); *C07K 2317/565* (2013.01); *C07K 2317/567* (2013.01); *C07K 2317/622* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,935,496 A | 6/1990 | Kudo et al. | |
| 5,502,167 A | 3/1996 | Waldmann et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,585,089 A | 12/1996 | Queen et al. | |
| 5,639,641 A | 6/1997 | Pedersen et al. | |
| 5,693,493 A | 12/1997 | Robinson et al. | |
| 5,693,761 A | 12/1997 | Queen et al. | |
| 5,693,762 A | 12/1997 | Queen et al. | |
| 5,698,417 A | 12/1997 | Robinson et al. | |
| 5,705,154 A | 1/1998 | Dalie et al. | |
| 5,733,743 A | 3/1998 | Johnson et al. | |
| 5,750,078 A | 5/1998 | Shitara et al. | |
| 5,770,403 A | 6/1998 | Dalie et al. | |
| 9,017,679 B2 | 4/2015 | Podack et al. | |
| 9,499,627 B2 | 11/2016 | Podack et al. | |
| 9,603,925 B2 | 3/2017 | Podack et al. | |
| 2007/0104715 A1 | 5/2007 | Nordstedt et al. | |
| 2007/0128184 A1 | 6/2007 | Podack et al. | |
| 2008/0003221 A1 | 1/2008 | Podack et al. | |
| 2009/0324600 A1 | 12/2009 | Haeuw et al. | |
| 2010/0092470 A1 | 4/2010 | Bhatt et al. | |
| 2011/0243951 A1 | 10/2011 | Podack et al. | |
| 2012/0014950 A1 | 1/2012 | Migone et al. | |
| 2012/0328559 A1 | 12/2012 | Podack et al. | |
| 2013/0251729 A1 | 9/2013 | Kuhne et al. | |
| 2013/0281922 A1 | 10/2013 | Teige | |
| 2014/0193410 A1 | 7/2014 | Podack et al. | |
| 2014/0286950 A1 | 9/2014 | Diehl et al. | |
| 2016/0015779 A1 | 1/2016 | Podack et al. | |
| 2017/0226218 A1 | 8/2017 | Podack et al. | |

FOREIGN PATENT DOCUMENTS

| | | |
|---|---|---|
| WO | WO2011/017303 | 2/2011 |
| WO | WO2016081455 | 5/2016 |

OTHER PUBLICATIONS

U.S. Appl. No. 15/618,993, filed Jun. 9, 2017, Podack et al.
Baldrick, "Toxicokinetics in Preclinical Evaluation", Pharmaceutical Excipient Development: The Need for Preclinical Guidance, Regulatory Toxicology and Pharmacology 32, 210-2108 (2000).
Bodmer et al., "TRAMP, A Novel Apoptosis-Mediating Receptor with Sequence Homology to Tumor Necrosis Factor Receptor 1 and Fas (Apo-1/CD95)", Immunity 6(1): 79-88, 1997.
Bu et al., "Expression and Function of TNF-Family Proteins and Receptors in Human Osteoblasts," Bone, 33(5); 760-770, (2003).
Cole et al., "The EBV-Hybridoma Technique and its Application to Human Lung Cancer," in Monocolonal Antibodies and Cancer Therapy, Alan R. Liss, Inc., pp. 77-96, 1983.
Cote et al., "Generation of Human Monoclonal Antibodies Reactive with Cellular Antigens," Proc. Natl. Acad. Sci.vol. 80, pp. 2026-2030, 1983.
Huse, et al., "Generation of a Large Combinatorial Library of the Immunoglobulin Repertoire in Phage Lambda," Science, 246; 1275, 1989.
International Preliminary Report on Patentability in International Application No. PCT/US2015/061082, dated May 23, 2017, 8 pages.
International Search Report and Written Opinion in International Application No. PCT/US2015/061082. dated Mar. 11, 2016, 8 pages.
Jones, et al., "Replacing the Complementarity—Determining Regions in a Human Antibody with Those From a Mouse," Nature, 321:522, 1986.

(Continued)

*Primary Examiner* — Daniel C Gamett
(74) *Attorney, Agent, or Firm* — Morgan, Lewis & Bockius LLP

(57) ABSTRACT

Anti-TNFRSF25 antibodies and variants thereof, including those that bind to an epitope in the region of amino acids 48-71, are disclosed. Also contemplated are uses of the antibodies in research, diagnostic, and therapeutic applications.

10 Claims, 16 Drawing Sheets

Specification includes a Sequence Listing.

(56) References Cited

OTHER PUBLICATIONS

Kitson et al., A Death-Domain-Containing Receptor That Mediates Apoptosls, Nature 384,6607; 372-375, 1996.

Kim et al., Treatment with agonistic DR3 antibody results in expansion of doner Tregs and reduced graft-versus-host disease, Blood, vol. 126(4); 546-557, 2015.

Kohler et al., "Continuous Cultures of fused Cells Secreting Antibody of Predefined Specificity," Nature 256; 495, 1975.

Konieczny, "The Combination of IgM subunits and Proteoilytic IgG fragments by controlled formation of Interchain Disulphides," Heamotaologia (Budap.) 14:95, 1981.

Kozbor and Roder, "The production of Monoclonal Antibodies from Human Lymphocytes," Immunology Today 4:72, 1983.

Kunkel, "Rapid and efficient site-specific mutagenesis without phenotypic selection," Proc Natl Acad Sci US'A 82(2):488-492, 1985.

Morrison et al, "ChimericHuman Antibody Molecules: Mouse Antigen-Binding domnans with Human Constant Region Domains," Proc Natl Acad Sci USA 81:6851-6855, 1984.

Powell et al., "Compendium of excipients for parental formulations," PDA J Pham Sci Technol 52:238-311, 1998.

Reddy et al, "TNFRSF25 agonistic antibody and Galectin-9 combination therapy controls herpes simplex virus-induced immunoimflamnatory lesions," J Virol 86; 19:10606-10620, 2012.

Riechmann et al., "Reshaping human antibodies for therapy," Nature 332:323, 1998.

Schreiber et al "Therapeutic Treg expansion in mice by TNFRSF25 prevent allergic lung inflammation," .J Clin Invest 120(10):3629-3640, 2010.

Schreiber et al., "T cell costimulation by TNFRSF4 and TNFRSF25 in the context of vaccination," J Immunol 189(7):3311-3318, 2010.

Wang, "Lyophilization and development of solid protein phannaceuticah," Int J Pham 203:1-60, 2000.

Wolf et al., "Tregs expanded in vivo by TNFRSF25 agonists promote cardiac allograft survival," Transplantation 94(6):569-574, 2012.

Chodorge et al., "A Series of Fas Receptor Agonist Antibodies that Demonstrate an Inverse Correlation Between Affinity and Potency", Cell Death and Differentiation, vol. 19, No. 7, 2012, pp. 1187-1195.

FIG. 1A

```
TNFRSF25    1                                         QGGTRSPRCDCAGDFHKKIGLECCRGCPAGHYLKAPCTEPCGNSTCLVC
TNFR1       1   YPSGVIGLVPHLGDRE.......    KRDSVCPQGKYIHPQNNSICCTKCHKGTYLYNDCPGPGQDTDCREC
Fas         1   RLSS.KSVNAQVTDINSKGLELRKTVTTVETQNLEGLHHDGQFCHKPCPPGERKARDCTVNGDEPDCVPC
                                          ┌──┐                                    ┌───┐
                                          │ I │                                    │III│
                                          └──┘                                    └───┘
TNFRSF25    50  PQDTFLAWENHHNSECARCQACDEQASQVALENCSAVADTRCGCKPGWFVECQVSQCVSSSPFYCQPCLD
TNFR1       63  ESGSFTASENHL.RHCLSCSKCRKEMGQVEISSCTVDRDTVCGCRKNQYRHYWSENL......FQCFNCSL
Fas         70  QEGKEYTDKAHFSSKCRRRCLCDEGHGLEVEINCTRTQNTKCRCKPNFF..CNSTVC.....EHCDPCTK
                                                ┌──┐
                                                │ II│
                                                └──┘
TNFRSF25    120 CGALHRHTRLLCS..RRDTDCGTCLLGFYEHGDGCVSCPTSTLGSCPE..RCAAVC..GWRQMFWVQ...
TNFR1       127 C..LNGTVHLSCQEKQNTVC.TCHAGFFLRENECVSC.....SNCKKSLECTKLCLPQIENVKGTEDSGT
Fas         133 C...EHGIIKECTLTSNTKC.KEEGSRSN..........
                                          ┌──┐
                                          │IV │
                                          └──┘
TNFRSF25    181 VLLAGLVVPLLLGATLTYTY....RHC.W.PHKPLVTADEAGMEALTPPPATHLSPLDSAHTLLAPPDSS
TNFR1       189 TVLLPLVIFFGLCLLSLLFIGLMYRYQRWKSKLYSIVCGKSTPEKEGELEGTTTKPLAPNPSFSPTPGFT
Fas         158 C...LGWLCLLLLPIPLIVWV.......KRKEVQKTCRKHRKENQGSHE.......
                ┌──┐
                │TM │
                └──┘
TNFRSF25    245 EKICTVQIVGNSWTPGYPETQEALCPQVTWSWDQLPSRALGPAA..APTLSPESPAGSPAMMLQP....
TNFR1       259 PTLGFSPVPSSTFTSSSSTYTPGD.CPNFAAPRREVAPPYQGADPILATALASDPIPNPLQKWEDSAHKPQ
Fas         196                        ............SPTLNPETVAINLSDVDL.......
                                                                    ┌──┐
                                                                    │DD │
                                                                    └──┘
TNFRSF25    308 .......GPQLYDVMDAVPARRWKEFVRTLGLREAEIEAVEVEIGR.FRDQQYEMLKRWRQQQPAGLG...
TNFR1       328 SLDTDDPATLYAVVENVPPLRWKEFVRRLGLSDHEIDRLELQNGRCLREAQYSMLATWRRRTPRREATLE
Fas         214 .......SKYITTIAGVMTLSQVKGFVRKNGVNEAKIDEIKNDNVQDTAEQKVQLLRNWHQLHGKKEA.YD

TNFRSF25    368 AVYAALERMGLDGCVEDLRSRLQRGP............     (SEQ ID NO:2)
TNFR1       398 LLGRVLRDMDLLGCLEDIEEALCGPAALPPAPSLLR......  (SEQ ID NO:3)
Fas         277 TLIKDLKKANLCTLAEKIQTIILKDITSDSENSNFRNEIQSLV (SEQ ID NO:4)
```

FIG. 1B

Human TNFRSF25 Sequence 1
Bodmer et al, Immunity 1997

MEQRPRGCAAVAAALLLVLLGARAQGSTRSPRCDCAGDFHKKIGLFCCRGCPAGHYLKAPCTEPCGNSTCLVCPQLTFLAW
ENHHNSECARCQACDEQASQVALENCSAVADTRCGCKPGWFVECQVSQCVSSSPFYCQPCLDCGALHRHTRLLCSRRDTDC
GTCLPGFYEHGDGCVSCPTSTLGSCPERCAAVCGWROMFWVQVLLAGLVVPLLLGATLTYTYRHCWPHKPLVTADEAGMEA
LTPPPATHLSPLDSAHTLLAPPDSSEKICTVQLVGNSWTPGYPETQEALCPQVTWSWDQLPSRALGPAAAPTLSPESPAGS
PAMMLQPGPQLYDVMDAVPARRWKEFVRTLGLREAEIEAVEVEIGRFRDQQYEMLKRWRQQQPAGLGAVYAALERMGLDGC
VEDLRSRLQRGP (SEQ ID NO:1)

Human TNFRSF25 Sequence 2
>gi|23200021|ref|NP_683866.1| tumor necrosis factor receptor superfamily member 25 isoform 1 precursor [Homo sapiens]

MEQRPRGCAAVAAALLLVLLGARAQGSTRSPRCDCAGDFHKKIGLFCCRGCPAGHYLKAPCTEPCGNSTCLVCPQLTFLAW
ENHHNSECARCQACDEQASQVALENCSAVADTRCGCKPGWFVECQVSQCVSSSPFYCQPCLDCGALHRHTRLLCSRRDTDC
GTCLPGFYEHGDGCVSCPTPPSLAGAPWGAVQSAVPLSVAGGRVGVFWVQVLLAGLVVPLLLGATLTYTYRHCWPHKPLV
TADEAGMEALTPPPATHLSPLDSAHTLLAPPDSSEKICTVQLVGNSWTPGYPETQEALCPQVTWSWDQLPSRALGPAAAPT
LSPESPAGSPAMMLQPGPQLYDVMDAVPARRWKEFVRTLGLREAEIEAVEVEIGRFRDQQYEMLKRWRQQQPAGLGAVYAA
LERMGLDGCVEDLRSRLQRGP (SEQ ID NO:7)

Mouse TNFRSF25 Sequence
>uc008vzk.1 (Tnfrsf25) length=387

MEELPRRERSPPGAATPGSTARVLQPLFLPLLLLLLLLGGQGQGGMSGRCDCASESQKRYGPFCCRGCPKGHYMKAPCAE
PCGNSTCLPCPSDTFLTRDNHFKTDCTRCQVCDEEALQVTLENCSAKSDTHCGCQSGWCVDCSTEPCGKSSPFSCVPCGAT
TPVHEAPTFLFWVQVLLGVAFLFGAILICAYCRWQPCKAVVTADTAGTETLASPQTAHLSASDSAHTLLAPPSSTGKICTT
VQLVGNNWTPGLSQTQEVVCGQASQPWDQLPNRTLGTPLASPLSPAPPAGSPAAVLQPGPQLYDVMDAVPARRWKEFVRTL
GLREAEIEAVEVEICRFRDQQYEMLKRWRQQQPAGLGAIYAALERMGLEGCAEDLRSRLQRGP (SEQ ID NO:8)

Rhesus Macaque TNFRSF25 Sequence
>gi|966914523|ref|XP_014998005.1|tumor necrosis factor receptor superfamily member 25 isoform X1 [Macaca mulatta]

MEQRSRGSAAVAAVSTALLLVLLGARAQGGTQSPRCDCAGDFHKKNGVFCCRGCPAGHYLKAPCTEPCGNSTCLLCPQDTF
LAWENHHNSECARCQACDEQASQVALENCSAVADTRCGCKPGWFVECQVSQCVSSSPFYCQPCLDCRALHRHTRLLCSFRD
TDCGTCLPGFYEHDDGCVSCPTSTLGSCPERCAAVCGWROMFWVQVLLAGLVVPLLLGATLTYTYRHCWPHKPMVTADEAG
MEALTPPPATHLSPSDKAHTLLVPPDSSEKICTVQLVDNSWTPGYPHTQEALCPQMTWSWDQLPNRALGPVPASTLLPESP
VGSPTMMLQPGPQLYDVMDAVPARRWKEFVRTLGLREAEIEAVEVEIGRFRDQQYEMLKRWRQQQPAGLGAVYAALERMGL
DGCAEDLRSRLQRGP (SEQ ID NO:9)

Cynomolgus Macaque TNFRSF25 Sequence
>gi|544409321|ref|XP_005544974.1| PREDICTED: tumor necrosis factor receptor superfamily member 25 isoform X2 [Macaca fascicularis]

MEQRSRGSAAVAAALLLVLLGARAQGGTQSPRCDCAGDFHKKNGVFCCRGCPAGHYLKAPCTEPCGNSTCLLCPQDTFLAW
ENHHNSECARCQACDEQASQVALENCSAVADTRCGCKPGWFVECQVSQCVSSSPFYCQPCLDCRALHRHTRLLCSRRDTDC
GTCLPGFYEHDDGCVSCPTSTLGSCPERCAAVCGWROMFWVQVLLAGLVVPLLLGATLTYTYRHCWPHKPMVTADEAGMEA
LTPPPATHLSPSDNAHTLLVPPDSSEKICTVQLVDNSWTPGYPHTQEALCPQMTWSWDQLPNRALGPVPASTLLPESPVGS
PTMMLQPGPQLYDVMDAVPARRWKEFVRTLGLREAEIEAVEVEIGRFRDQQYEMLKRWRQQQPAGLGAVYAALERMGLDGC
AEDLRSRLQRGP (SEQ ID NO:10)

<u>Underlined</u> = Signal Peptide
Highlighted = Extracellular Domain
Bold = Transmembrane Domain
<u>Double Underlined</u> = PTX25 Epitope

SEQUENCE LISTING

<160> NUMBER OF SEQ ID NOS: 35

<210> SEQ ID NO 1
<211> LENGTH: 417
<212> TYPE: PRT
<213> ORGANISM: Homo sapiens

<400> SEQUENCE: 1

Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro

```
            50                  55                  60
Cys Gly Asn Ser Thr Cys Leu Val Cys Pro Gln Asp Thr Phe Leu Ala
 65                  70                  75                  80

Trp Glu Asn His His Asn Ser Glu Cys Ala Arg Cys Gln Ala Cys Asp
                 85                  90                  95

Glu Gln Ala Ser Gln Val Ala Leu Glu Asn Cys Ser Ala Val Ala Asp
                100                 105                 110

Thr Arg Cys Gly Cys Lys Pro Gly Trp Phe Val Glu Cys Gln Val Ser
                115                 120                 125

Gln Cys Val Ser Ser Pro Phe Tyr Cys Gln Pro Cys Leu Asp Cys
            130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
            195                 200                 205

Gly Leu Val Val Pro Leu Leu Leu Gly Ala Thr Leu Thr Tyr Thr Tyr
210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
                260                 265                 270

Thr Val Gln Leu Val Gly Asn Ser Trp Thr Pro Gly Tyr Pro Glu Thr
            275                 280                 285

Gln Glu Ala Leu Cys Pro Gln Val Thr Trp Ser Trp Asp Gln Leu Pro
            290                 295                 300

Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
                340                 345                 350

Thr Leu Gly Leu Arg Glu Ala Glu Ile Glu Ala Val Glu Val Glu Ile
                355                 360                 365

Gly Arg Phe Arg Asp Gln Gln Tyr Glu Met Leu Lys Arg Trp Arg Gln
370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 2
<211> LENGTH: 393
<212> TYPE: PRT
<213> ORGANISM: Homo sapiens

<400> SEQUENCE: 2

Gln Gly Gly Thr Arg Ser Pro Arg Cys Asp Cys Ala Gly Asp Phe His
```

```
           1               5                  10                 15
Lys Lys Ile Gly Leu Phe Cys Cys Arg Gly Cys Pro Ala Gly His Tyr
                20                 25                 30

Leu Lys Ala Pro Cys Thr Glu Pro Cys Gly Asn Ser Thr Cys Leu Val
                35                 40                 45

Cys Pro Gln Asp Thr Phe Leu Ala Trp Glu Asn His Asn Ser Glu
 50                 55                 60

Cys Ala Arg Cys Gln Ala Cys Asp Glu Gln Ala Ser Gln Val Ala Leu
 65                 70                 75                 80

Glu Asn Cys Ser Ala Val Ala Asp Thr Arg Cys Gly Cys Lys Pro Gly
                85                 90                 95

Trp Phe Val Glu Cys Gln Val Ser Gln Cys Val Ser Ser Pro Phe
                100                105                110

Tyr Cys Gln Pro Cys Leu Asp Cys Gly Ala Leu His Arg His Thr Arg
                115                120                125

Leu Leu Cys Ser Arg Arg Asp Thr Asp Cys Gly Thr Cys Leu Leu Gly
 130                135                140

Phe Tyr Glu His Gly Asp Gly Cys Val Ser Cys Pro Thr Ser Thr Leu
 145                150                155                160

Gly Ser Cys Pro Glu Arg Cys Ala Ala Val Cys Gly Trp Arg Gln Met
                165                170                175

Phe Trp Val Gln Val Leu Leu Ala Gly Leu Val Val Pro Leu Leu Leu
                180                185                190

Gly Ala Thr Leu Thr Tyr Thr Tyr Arg His Cys Trp Pro His Lys Pro
                195                200                205

Leu Val Thr Ala Asp Glu Ala Gly Met Glu Ala Leu Thr Pro Pro Pro
 210                215                220

Ala Thr His Leu Ser Pro Leu Asp Ser Ala His Thr Leu Leu Ala Pro
 225                230                235                240

Pro Asp Ser Ser Glu Lys Ile Cys Thr Val Gln Leu Val Gly Asn Ser
                245                250                255

Trp Thr Pro Gly Tyr Pro Glu Thr Gln Glu Ala Leu Cys Pro Gln Val
                260                265                270

Thr Trp Ser Trp Asp Gln Leu Pro Ser Arg Ala Leu Gly Pro Ala Ala
                275                280                285

Ala Pro Thr Leu Ser Pro Glu Ser Pro Ala Gly Ser Pro Ala Met Met
 290                295                300

Leu Gln Pro Gly Pro Gln Leu Tyr Asp Val Met Asp Ala Val Pro Ala
 305                310                315                320

Arg Arg Trp Lys Glu Phe Val Arg Thr Leu Gly Leu Arg Glu Ala Glu
                325                330                335

Ile Glu Ala Val Glu Val Glu Ile Gly Arg Phe Arg Asp Gln Gln Tyr
                340                345                350

Glu Met Leu Lys Arg Trp Arg Gln Gln Pro Ala Gly Leu Gly Ala
                355                360                365

Val Tyr Ala Ala Leu Glu Arg Met Gly Leu Asp Gly Cys Val Glu Asp
 370                375                380

Leu Arg Ser Arg Leu Gln Arg Gly Pro
 385                390

<210> SEQ ID NO 3
<211> LENGTH: 433
<212> TYPE: PRT
<213> ORGANISM: Homo sapiens
```

<400> SEQUENCE: 3

```
Tyr Pro Ser Gly Val Ile Gly Leu Val Pro His Leu Gly Asp Arg Glu
1               5                   10                  15

Lys Arg Asp Ser Val Cys Pro Gln Gly Lys Tyr Ile His Pro Gln Asn
            20                  25                  30

Asn Ser Ile Cys Cys Thr Lys Cys His Lys Gly Thr Tyr Leu Tyr Asn
        35                  40                  45

Asp Cys Pro Gly Pro Gly Gln Asp Thr Asp Cys Arg Glu Cys Glu Ser
    50                  55                  60

Gly Ser Phe Thr Ala Ser Glu Asn His Leu Arg His Cys Leu Ser Cys
65                  70                  75                  80

Ser Lys Cys Arg Lys Glu Met Gly Gln Val Glu Ile Ser Ser Cys Thr
                85                  90                  95

Val Asp Arg Asp Thr Val Cys Gly Cys Arg Lys Asn Gln Tyr Arg His
                100                 105                 110

Tyr Trp Ser Glu Asn Leu Phe Gln Cys Phe Asn Cys Ser Leu Cys Leu
            115                 120                 125

Asn Gly Thr Val His Leu Ser Cys Gln Glu Lys Gln Asn Thr Val Cys
        130                 135                 140

Thr Cys His Ala Gly Phe Phe Leu Arg Glu Asn Glu Cys Val Ser Cys
145                 150                 155                 160

Ser Asn Cys Lys Lys Ser Leu Glu Cys Thr Lys Leu Cys Leu Pro Gln
                165                 170                 175

Ile Glu Asn Val Lys Gly Thr Glu Asp Ser Gly Thr Thr Val Leu Leu
                180                 185                 190

Pro Leu Val Ile Phe Phe Gly Leu Cys Leu Leu Ser Leu Leu Phe Ile
            195                 200                 205

Gly Leu Met Tyr Arg Tyr Gln Arg Trp Lys Ser Lys Leu Tyr Ser Ile
        210                 215                 220

Val Cys Gly Lys Ser Thr Pro Glu Lys Glu Gly Glu Leu Glu Gly Thr
225                 230                 235                 240

Thr Thr Lys Pro Leu Ala Pro Asn Pro Ser Phe Ser Pro Thr Pro Gly
                245                 250                 255

Phe Thr Pro Thr Leu Gly Phe Ser Pro Val Pro Ser Ser Thr Phe Thr
            260                 265                 270

Ser Ser Ser Thr Tyr Thr Pro Gly Asp Cys Pro Asn Phe Ala Ala Pro
        275                 280                 285

Arg Arg Glu Val Ala Pro Pro Tyr Gln Gly Ala Asp Pro Ile Leu Ala
290                 295                 300

Thr Ala Leu Ala Ser Asp Pro Ile Pro Asn Pro Leu Gln Lys Trp Glu
305                 310                 315                 320

Asp Ser Ala His Lys Pro Gln Ser Leu Asp Thr Asp Pro Ala Thr
                325                 330                 335

Leu Tyr Ala Val Val Glu Asn Val Pro Pro Leu Arg Trp Lys Glu Phe
            340                 345                 350

Val Arg Arg Leu Gly Leu Ser Asp His Glu Ile Asp Arg Leu Glu Leu
        355                 360                 365

Gln Asn Gly Arg Cys Leu Arg Glu Ala Gln Tyr Ser Met Leu Ala Thr
    370                 375                 380

Trp Arg Arg Arg Thr Pro Arg Arg Glu Ala Thr Leu Glu Leu Leu Gly
385                 390                 395                 400

Arg Val Leu Arg Asp Met Asp Leu Leu Gly Cys Leu Glu Asp Ile Glu
```

```
                    405                 410                 415

Glu Ala Leu Cys Gly Pro Ala Ala Leu Pro Pro Ala Pro Ser Leu Leu
                420                 425                 430

Arg

<210> SEQ ID NO 4
<211> LENGTH: 319
<212> TYPE: PRT
<213> ORGANISM: Homo sapiens

<400> SEQUENCE: 4

Arg Leu Ser Ser Lys Ser Val Asn Ala Gln Val Thr Asp Ile Asn Ser
1               5                   10                  15

Lys Gly Leu Glu Leu Arg Lys Thr Val Thr Val Glu Thr Gln Asn
            20                  25                  30

Leu Glu Gly Leu His His Asp Gly Gln Phe Cys His Lys Pro Cys Pro
        35                  40                  45

Pro Gly Glu Arg Lys Ala Arg Asp Cys Thr Val Asn Gly Asp Glu Pro
    50                  55                  60

Asp Cys Val Pro Cys Gln Glu Gly Lys Glu Tyr Thr Asp Lys Ala His
65                  70                  75                  80

Phe Ser Ser Lys Cys Arg Arg Cys Arg Leu Cys Asp Glu Gly His Gly
                85                  90                  95

Leu Glu Val Glu Ile Asn Cys Thr Arg Thr Gln Asn Thr Lys Cys Arg
            100                 105                 110

Cys Lys Pro Asn Phe Phe Cys Asn Ser Thr Val Cys Glu His Cys Asp
        115                 120                 125

Pro Cys Thr Lys Cys Glu His Gly Ile Ile Lys Glu Cys Thr Leu Thr
    130                 135                 140

Ser Asn Thr Lys Cys Lys Glu Glu Gly Ser Arg Ser Asn Leu Gly Trp
145                 150                 155                 160

Leu Cys Leu Leu Leu Leu Pro Ile Pro Leu Ile Val Trp Val Lys Arg
                165                 170                 175

Lys Glu Val Gln Lys Thr Cys Arg Lys His Arg Lys Glu Asn Gln Gly
            180                 185                 190

Ser His Glu Ser Pro Thr Leu Asn Pro Glu Thr Val Ala Ile Asn Leu
        195                 200                 205

Ser Asp Val Asp Leu Ser Lys Tyr Ile Thr Thr Ile Ala Gly Val Met
    210                 215                 220

Thr Leu Ser Gln Val Lys Gly Phe Val Arg Lys Asn Gly Val Asn Glu
225                 230                 235                 240

Ala Lys Ile Asp Glu Ile Lys Asn Asp Asn Val Gln Asp Thr Ala Glu
                245                 250                 255

Gln Lys Val Gln Leu Leu Arg Asn Trp His Gln Leu His Gly Lys Lys
            260                 265                 270

Glu Ala Tyr Asp Thr Leu Ile Lys Asp Leu Lys Lys Ala Asn Leu Cys
        275                 280                 285

Thr Leu Ala Glu Lys Ile Gln Thr Ile Ile Leu Lys Asp Ile Thr Ser
    290                 295                 300

Asp Ser Glu Asn Ser Asn Phe Arg Asn Glu Ile Gln Ser Leu Val
305                 310                 315

<210> SEQ ID NO 5
<211> LENGTH: 121
<212> TYPE: PRT
```

<213> ORGANISM: Cricetulus migratorius

<400> SEQUENCE: 5

Glu Val Gln Leu Val Glu Ser Gly Gly Gly Leu Ser Gln Pro Gly Asn
1               5                   10                  15

Ser Leu Gln Leu Ser Cys Glu Ala Ser Gly Phe Thr Phe Ser Asn His
            20                  25                  30

Asp Leu Asn Trp Val Arg Gln Ala Pro Gly Lys Gly Leu Glu Trp Val
        35                  40                  45

Ala Tyr Ile Ser Ser Ala Ser Gly Leu Ile Ser Tyr Ala Asp Ala Val
    50                  55                  60

Arg Gly Arg Phe Thr Ile Ser Arg Asp Asn Ala Lys Asn Ser Leu Phe
65                  70                  75                  80

Leu Gln Met Asn Asn Leu Lys Ser Glu Asp Thr Ala Met Tyr Tyr Cys
                85                  90                  95

Ala Arg Asp Pro Pro Tyr Ser Gly Leu Tyr Ala Leu Asp Phe Trp Gly
            100                 105                 110

Gln Gly Thr Gln Val Thr Val Ser Ser
        115                 120

<210> SEQ ID NO 6
<211> LENGTH: 115
<212> TYPE: PRT
<213> ORGANISM: Cricetulus migratorius

<400> SEQUENCE: 6

Gln Pro Val Leu Thr Gln Ser Pro Ser Ala Ser Ala Ser Leu Ser Gly
1               5                   10                  15

Ser Val Lys Leu Thr Cys Thr Leu Ser Ser Glu Leu Ser Ser Tyr Thr
            20                  25                  30

Ile Val Trp Tyr Gln Gln Arg Pro Asp Lys Ala Pro Lys Tyr Val Met
        35                  40                  45

Tyr Leu Lys Ser Asp Gly Ser His Ser Lys Gly Asp Gly Ile Pro Asp
    50                  55                  60

Arg Phe Ser Gly Ser Ser Ser Gly Ala His Arg Tyr Leu Ser Ile Ser
65                  70                  75                  80

Asn Val Gln Ser Glu Asp Asp Ala Thr Tyr Phe Cys Gly Ala Gly Tyr
                85                  90                  95

Thr Leu Ala Gly Gln Tyr Gly Trp Val Phe Gly Ser Gly Thr Lys Val
            100                 105                 110

Thr Val Leu
        115

<210> SEQ ID NO 7
<211> LENGTH: 426
<212> TYPE: PRT
<213> ORGANISM: Homo sapiens

<400> SEQUENCE: 7

Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

```
Cys Gly Asn Ser Thr Cys Leu Val Cys Pro Gln Asp Thr Phe Leu Ala
 65                  70                  75                  80

Trp Glu Asn His His Asn Ser Glu Cys Ala Arg Cys Gln Ala Cys Asp
             85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Pro Pro Ser Leu Ala Gly Ala Pro Trp Gly
            180                 185                 190

Ala Val Gln Ser Ala Val Pro Leu Ser Val Ala Gly Arg Val Gly
        195                 200                 205

Val Phe Trp Val Gln Val Leu Leu Ala Gly Leu Val Val Pro Leu Leu
    210                 215                 220

Leu Gly Ala Thr Leu Thr Tyr Thr Tyr Arg His Cys Trp Pro His Lys
225                 230                 235                 240

Pro Leu Val Thr Ala Asp Glu Ala Gly Met Glu Ala Leu Thr Pro Pro
                245                 250                 255

Pro Ala Thr His Leu Ser Pro Leu Asp Ser Ala His Thr Leu Leu Ala
            260                 265                 270

Pro Pro Asp Ser Ser Glu Lys Ile Cys Thr Val Gln Leu Val Gly Asn
        275                 280                 285

Ser Trp Thr Pro Gly Tyr Pro Glu Thr Gln Glu Ala Leu Cys Pro Gln
    290                 295                 300

Val Thr Trp Ser Trp Asp Gln Leu Pro Ser Arg Ala Leu Gly Pro Ala
305                 310                 315                 320

Ala Ala Pro Thr Leu Ser Pro Glu Ser Pro Ala Gly Ser Pro Ala Met
                325                 330                 335

Met Leu Gln Pro Gly Pro Gln Leu Tyr Asp Val Met Asp Ala Val Pro
            340                 345                 350

Ala Arg Arg Trp Lys Glu Phe Val Arg Thr Leu Gly Leu Arg Glu Ala
        355                 360                 365

Glu Ile Glu Ala Val Glu Val Glu Ile Gly Arg Phe Arg Asp Gln Gln
    370                 375                 380

Tyr Glu Met Leu Lys Arg Trp Arg Gln Gln Pro Ala Gly Leu Gly
385                 390                 395                 400

Ala Val Tyr Ala Ala Leu Glu Arg Met Gly Leu Asp Gly Cys Val Glu
                405                 410                 415

Asp Leu Arg Ser Arg Leu Gln Arg Gly Pro
            420                 425

<210> SEQ ID NO 8
<211> LENGTH: 387
<212> TYPE: PRT
<213> ORGANISM: Mus musculus

<400> SEQUENCE: 8

Met Glu Glu Leu Pro Arg Arg Glu Arg Ser Pro Pro Gly Ala Ala Thr
```

```
1               5                   10                  15
    Pro Gly Ser Thr Ala Arg Val Leu Gln Pro Leu Phe Leu Pro Leu Leu
                    20                  25                  30

Leu Leu Leu Leu Leu Leu Leu Gly Gly Gln Gly Gln Gly Gly Met Ser
                    35                  40                  45

Gly Arg Cys Asp Cys Ala Ser Glu Ser Gln Lys Arg Tyr Gly Pro Phe
    50                  55                  60

Cys Cys Arg Gly Cys Pro Lys Gly His Tyr Met Lys Ala Pro Cys Ala
    65                  70                  75                  80

Glu Pro Cys Gly Asn Ser Thr Cys Leu Pro Cys Pro Ser Asp Thr Phe
                    85                  90                  95

Leu Thr Arg Asp Asn His Phe Lys Thr Asp Cys Thr Arg Cys Gln Val
                    100                 105                 110

Cys Asp Glu Glu Ala Leu Gln Val Thr Leu Glu Asn Cys Ser Ala Lys
                    115                 120                 125

Ser Asp Thr His Cys Gly Cys Gln Ser Gly Trp Cys Val Asp Cys Ser
                    130                 135                 140

Thr Glu Pro Cys Gly Lys Ser Ser Pro Phe Ser Cys Val Pro Cys Gly
    145                 150                 155                 160

Ala Thr Thr Pro Val His Glu Ala Pro Thr Pro Leu Phe Trp Val Gln
                    165                 170                 175

Val Leu Leu Gly Val Ala Phe Leu Phe Gly Ala Ile Leu Ile Cys Ala
                    180                 185                 190

Tyr Cys Arg Trp Gln Pro Cys Lys Ala Val Val Thr Ala Asp Thr Ala
                    195                 200                 205

Gly Thr Glu Thr Leu Ala Ser Pro Gln Thr Ala His Leu Ser Ala Ser
                    210                 215                 220

Asp Ser Ala His Thr Leu Leu Ala Pro Pro Ser Ser Thr Gly Lys Ile
    225                 230                 235                 240

Cys Thr Thr Val Gln Leu Val Gly Asn Asn Trp Thr Pro Gly Leu Ser
                    245                 250                 255

Gln Thr Gln Glu Val Val Cys Gly Gln Ala Ser Gln Pro Trp Asp Gln
                    260                 265                 270

Leu Pro Asn Arg Thr Leu Gly Thr Pro Leu Ala Ser Pro Leu Ser Pro
                    275                 280                 285

Ala Pro Pro Ala Gly Ser Pro Ala Ala Val Leu Gln Pro Gly Pro Gln
                    290                 295                 300

Leu Tyr Asp Val Met Asp Ala Val Pro Ala Arg Arg Trp Lys Glu Phe
    305                 310                 315                 320

Val Arg Thr Leu Gly Leu Arg Glu Ala Glu Ile Glu Ala Val Glu Val
                    325                 330                 335

Glu Ile Cys Arg Phe Arg Asp Gln Gln Tyr Glu Met Leu Lys Arg Trp
                    340                 345                 350

Arg Gln Gln Gln Pro Ala Gly Leu Gly Ala Ile Tyr Ala Ala Leu Glu
                    355                 360                 365

Arg Met Gly Leu Glu Gly Cys Ala Glu Asp Leu Arg Ser Arg Leu Gln
                    370                 375                 380

Arg Gly Pro
    385

<210> SEQ ID NO 9
<211> LENGTH: 420
<212> TYPE: PRT
<213> ORGANISM: Macaca mulatta
```

```
<400> SEQUENCE: 9

Met Glu Gln Arg Ser Arg Gly Ser Ala Ala Val Ala Val Ser Thr
1               5                   10                  15

Ala Leu Leu Val Leu Leu Gly Ala Arg Ala Gln Gly Gly Thr Gln
                20                  25                  30

Ser Pro Arg Cys Asp Cys Ala Gly Asp Phe His Lys Lys Asn Gly Val
            35                  40                  45

Phe Cys Cys Arg Gly Cys Pro Ala Gly His Tyr Leu Lys Ala Pro Cys
    50                  55                  60

Thr Glu Pro Cys Gly Asn Ser Thr Cys Leu Leu Cys Pro Gln Asp Thr
65                  70                  75                  80

Phe Leu Ala Trp Glu Asn His His Asn Ser Glu Cys Ala Arg Cys Gln
                85                  90                  95

Ala Cys Asp Glu Gln Ala Ser Gln Val Ala Leu Glu Asn Cys Ser Ala
                100                 105                 110

Val Ala Asp Thr Arg Cys Gly Cys Lys Pro Gly Trp Phe Val Glu Cys
                115                 120                 125

Gln Val Ser Gln Cys Val Ser Ser Pro Phe Tyr Cys Gln Pro Cys
130                 135                 140

Leu Asp Cys Arg Ala Leu His Arg His Thr Arg Leu Leu Cys Ser Arg
145                 150                 155                 160

Arg Asp Thr Asp Cys Gly Thr Cys Leu Pro Gly Phe Tyr Glu His Asp
                165                 170                 175

Asp Gly Cys Val Ser Cys Pro Thr Ser Thr Leu Gly Ser Cys Pro Glu
                180                 185                 190

Arg Cys Ala Ala Val Cys Gly Trp Arg Gln Met Phe Trp Val Gln Val
                195                 200                 205

Leu Leu Ala Gly Leu Val Val Pro Leu Leu Leu Gly Ala Thr Leu Thr
210                 215                 220

Tyr Thr Tyr Arg His Cys Trp Pro His Lys Pro Met Val Thr Ala Asp
225                 230                 235                 240

Glu Ala Gly Met Glu Ala Leu Thr Pro Pro Ala Thr His Leu Ser
                245                 250                 255

Pro Ser Asp Lys Ala His Thr Leu Leu Val Pro Pro Asp Ser Ser Glu
                260                 265                 270

Lys Ile Cys Thr Val Gln Leu Val Asp Asn Ser Trp Thr Pro Gly Tyr
            275                 280                 285

Pro His Thr Gln Glu Ala Leu Cys Pro Gln Met Thr Trp Ser Trp Asp
            290                 295                 300

Gln Leu Pro Asn Arg Ala Leu Gly Pro Val Pro Ala Ser Thr Leu Leu
305                 310                 315                 320

Pro Glu Ser Pro Val Gly Ser Pro Thr Met Met Leu Gln Pro Gly Pro
                325                 330                 335

Gln Leu Tyr Asp Val Met Asp Ala Val Pro Ala Arg Arg Trp Lys Glu
                340                 345                 350

Phe Val Arg Thr Leu Gly Leu Arg Glu Ala Glu Ile Glu Ala Val Glu
                355                 360                 365

Val Glu Ile Gly Arg Phe Arg Asp Gln Gln Tyr Glu Met Leu Lys Arg
            370                 375                 380

Trp Arg Gln Gln Gln Pro Ala Gly Leu Gly Ala Val Tyr Ala Ala Leu
385                 390                 395                 400

Glu Arg Met Gly Leu Asp Gly Cys Ala Glu Asp Leu Arg Ser Arg Leu
```

Gln Arg Gly Pro
            420

<210> SEQ ID NO 10
<211> LENGTH: 417
<212> TYPE: PRT
<213> ORGANISM: Macaca fascicularis

<400> SEQUENCE: 10

Met Glu Gln Arg Ser Arg Gly Ser Ala Ala Val Ala Ala Ala Leu Leu
1               5                   10                  15

Leu Val Leu Leu Gly Ala Arg Ala Gln Gly Thr Gln Ser Pro Arg
            20                  25                  30

Cys Asp Cys Ala Gly Asp Phe His Lys Lys Asn Gly Val Phe Cys Cys
            35                  40                  45

Arg Gly Cys Pro Ala Gly His Tyr Leu Lys Ala Pro Cys Thr Glu Pro
50                  55                  60

Cys Gly Asn Ser Thr Cys Leu Leu Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
            115                 120                 125

Gln Cys Gly Ser Ser Pro Phe Tyr Cys Gln Pro Cys Leu Asp Cys
130                 135                 140

Arg Ala Leu His Arg His Thr Arg Leu Leu Cys Ser Arg Arg Asp Thr
145                 150                 155                 160

Asp Cys Gly Thr Cys Leu Pro Gly Phe Tyr Glu His Asp Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
            195                 200                 205

Gly Leu Val Val Pro Leu Leu Leu Gly Ala Thr Leu Thr Tyr Thr Tyr
210                 215                 220

Arg His Cys Trp Pro His Lys Pro Met Val Thr Ala Asp Glu Ala Gly
225                 230                 235                 240

Met Glu Ala Leu Thr Pro Pro Ala Thr His Leu Ser Pro Ser Asp
                245                 250                 255

Asn Ala His Thr Leu Leu Val Pro Pro Asp Ser Ser Glu Lys Ile Cys
            260                 265                 270

Thr Val Gln Leu Val Asp Asn Ser Trp Thr Pro Gly Tyr Pro His Thr
            275                 280                 285

Gln Glu Ala Leu Cys Pro Gln Met Thr Trp Ser Trp Asp Gln Leu Pro
        290                 295                 300

Asn Arg Ala Leu Gly Pro Val Pro Ala Ser Thr Leu Leu Pro Glu Ser
305                 310                 315                 320

Pro Val Gly Ser Pro Thr Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

```
Thr Leu Gly Leu Arg Glu Ala Glu Ile Glu Ala Val Glu Val Glu Ile
            355                 360                 365

Gly Arg Phe Arg Asp Gln Gln Tyr Glu Met Leu Lys Arg Trp Arg Gln
        370                 375                 380

Gln Gln Pro Ala Gly Leu Gly Ala Val Tyr Ala Ala Leu Glu Arg Met
385                 390                 395                 400

Gly Leu Asp Gly Cys Ala Glu Asp Leu Arg Ser Arg Leu Gln Arg Gly
                405                 410                 415

Pro

<210> SEQ ID NO 11
<211> LENGTH: 25
<212> TYPE: PRT
<213> ORGANISM: Cricetulus migratorius

<400> SEQUENCE: 11

Glu Val Gln Leu Val Glu Ser Gly Gly Gly Leu Ser Gln Pro Gly Asn
1               5                   10                  15

Ser Leu Gln Leu Ser Cys Glu Ala Ser
            20                  25

<210> SEQ ID NO 12
<211> LENGTH: 10
<212> TYPE: PRT
<213> ORGANISM: Cricetulus migratorius

<400> SEQUENCE: 12

Gly Phe Thr Phe Ser Asn His Asp Leu Asn
1               5                   10

<210> SEQ ID NO 13
<211> LENGTH: 14
<212> TYPE: PRT
<213> ORGANISM: Cricetulus migratorius

<400> SEQUENCE: 13

Trp Val Arg Gln Ala Pro Gly Lys Gly Leu Glu Trp Val Ala
1               5                   10

<210> SEQ ID NO 14
<211> LENGTH: 17
<212> TYPE: PRT
<213> ORGANISM: Cricetulus migratorius

<400> SEQUENCE: 14

Tyr Ile Ser Ser Ala Ser Gly Leu Ile Ser Tyr Ala Asp Ala Val Arg
1               5                   10                  15

Gly

<210> SEQ ID NO 15
<211> LENGTH: 32
<212> TYPE: PRT
<213> ORGANISM: Cricetulus migratorius

<400> SEQUENCE: 15

Arg Phe Thr Ile Ser Arg Asp Asn Ala Lys Asn Ser Leu Phe Leu Gln
1               5                   10                  15

Met Asn Asn Leu Lys Ser Glu Asp Thr Ala Met Tyr Tyr Cys Ala Arg
            20                  25                  30

<210> SEQ ID NO 16
```

```
<211> LENGTH: 12
<212> TYPE: PRT
<213> ORGANISM: Cricetulus migratorius

<400> SEQUENCE: 16

Asp Pro Pro Tyr Ser Gly Leu Tyr Ala Leu Asp Phe
1               5                   10

<210> SEQ ID NO 17
<211> LENGTH: 11
<212> TYPE: PRT
<213> ORGANISM: Cricetulus migratorius

<400> SEQUENCE: 17

Trp Gly Gln Gly Thr Gln Val Thr Val Ser Ser
1               5                   10

<210> SEQ ID NO 18
<211> LENGTH: 22
<212> TYPE: PRT
<213> ORGANISM: Cricetulus migratorius

<400> SEQUENCE: 18

Gln Pro Val Leu Thr Gln Ser Pro Ser Ala Ser Ala Ser Leu Ser Gly
1               5                   10                  15

Ser Val Lys Leu Thr Cys
            20

<210> SEQ ID NO 19
<211> LENGTH: 12
<212> TYPE: PRT
<213> ORGANISM: Cricetulus migratorius

<400> SEQUENCE: 19

Thr Leu Ser Ser Glu Leu Ser Ser Tyr Thr Ile Val
1               5                   10

<210> SEQ ID NO 20
<211> LENGTH: 15
<212> TYPE: PRT
<213> ORGANISM: Cricetulus migratorius

<400> SEQUENCE: 20

Trp Tyr Gln Gln Arg Pro Asp Lys Ala Pro Lys Tyr Val Met Tyr
1               5                   10                  15

<210> SEQ ID NO 21
<211> LENGTH: 11
<212> TYPE: PRT
<213> ORGANISM: Cricetulus migratorius

<400> SEQUENCE: 21

Leu Lys Ser Asp Gly Ser His Ser Lys Gly Asp
1               5                   10

<210> SEQ ID NO 22
<211> LENGTH: 31
<212> TYPE: PRT
<213> ORGANISM: Cricetulus migratorius

<400> SEQUENCE: 22

Gly Ile Pro Asp Arg Phe Ser Gly Ser Ser Gly Ala His Arg Tyr
1               5                   10                  15

Leu Ser Ile Ser Asn Val Gln Ser Glu Asp Asp Ala Thr Tyr Phe
```

<210> SEQ ID NO 23
<211> LENGTH: 14
<212> TYPE: PRT
<213> ORGANISM: Cricetulus migratorius

<400> SEQUENCE: 23

Cys Gly Ala Gly Tyr Thr Leu Ala Gly Gln Tyr Gly Trp Val
1               5                   10

<210> SEQ ID NO 24
<211> LENGTH: 10
<212> TYPE: PRT
<213> ORGANISM: Cricetulus migratorius

<400> SEQUENCE: 24

Phe Gly Ser Gly Thr Lys Val Thr Val Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic

<400> SEQUENCE: 25

Thr Leu Ser Ser Glu Leu Ser Trp Tyr Thr Ile Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic

<400> SEQUENCE: 26

Asp Pro Ala Tyr Thr Gly Leu Tyr Ala Leu Asp Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic

<400> SEQUENCE: 27

Thr Leu Ser Ser Glu Leu Ser Gly Phe Thr Ile Val
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic

<400> SEQUENCE: 28

Cys Gly Ala Gly Tyr Thr Leu Ala Asn Gln Tyr Gly Trp Val
1               5                   10

<210> SEQ ID NO 29
<211> LENGTH: 12

<212> TYPE: PRT
<213> ORGANISM: Artificial Sequence
<220> FEATURE:
<223> OTHER INFORMATION: synthetic

<400> SEQUENCE: 29

Thr Leu Ser Ser Glu Leu Ser Asn Phe Thr Ile Val
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic

<400> SEQUENCE: 30

Cys Gly Ala Gly Tyr Thr Leu Ala Ser Gln Tyr Gly Trp Val
1               5                   10

<210> SEQ ID NO 31
<211> LENGTH: 12
<212> TYPE: PRT
<213> ORGANISM: Artificial Sequence
<220> FEATURE:
<223> OTHER INFORMATION: synthetic

<400> SEQUENCE: 31

Asp Pro Ala Tyr Ser Gly Leu Tyr Ala Leu Asp Phe
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic

<400> SEQUENCE: 32

Asp Pro Pro Tyr Thr Gly Leu Tyr Ala Leu Asp Phe
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic

<400> SEQUENCE: 33

Thr Leu Ser Ser Glu Leu Ser Asn Tyr Thr Ile Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic

<400> SEQUENCE: 34

Cys Gly Ala Gly Tyr Thr Leu Ala Arg Gln Tyr Gly Trp Val
1               5                   10

<210> SEQ ID NO 35
<211> LENGTH: 14
<212> TYPE: PRT

```
<213> ORGANISM: Artificial Sequence
<220> FEATURE:
<223> OTHER INFORMATION: synthetic

<400> SEQUENCE: 35

Cys Gly Met Gly Tyr Thr Leu Ala Asn Gln Tyr Gly Trp Val
1               5                   10
```

ANTI-TNFRSF25 ANTIBODIES

CROSS-REFERENCE TO RELATED APPLICATIONS

This application claims benefit of priority from U.S. Provisional Application Ser. No. 62/348,009, filed on Jun. 9, 2016.

TECHNICAL FIELD

This document relates to anti-TNFRSF25 antibodies, and to their use in research, therapeutic, and diagnostic purposes.

BACKGROUND

Tumor necrosis factor receptor superfamily member 25 (TNFRSF25) is a TNF-receptor superfamily member that is preferentially expressed by activated and antigen-experienced T lymphocytes. TNFRSF25 is activated by its ligand, TL1A (also called TNFSF15), which is rapidly upregulated in antigen presenting cells and in some endothelial cells following Toll-Like Receptor or Fc receptor activation. TNFRSF25 can stimulate NF-kappa B activity, and also can stimulate caspase activation to regulate cell apoptosis (Bodmer et al., *Immunity* 6(1):79-88, 1997; and Kitson et al., *Nature* 384(6607):372-375, 1996). The structural organization of the 393 amino acid long human TNFRSF25 protein is most homologous to TNF receptor 1 (TNFR1). The extracellular domain of TNFRSF25 includes four cysteine-rich domains, and the cytoplasmic region contains a death domain known to signal apoptosis. Alternative splicing produces multiple distinct isoforms of TNFRSF25, most of which are potentially secreted molecules. Alternative splicing of the TNFRSF25 gene in B and T cells encounters a program change upon T-cell activation, which predominantly produces full-length, membrane bound isoforms, and is thought to be involved in controlling lymphocyte proliferation induced by T-cell activation.

Activation of TNFRSF25 is dependent on previous engagement of the T cell receptor. After binding of TNARSF25 to TL1A, TNFRSF25 signaling increases the sensitivity of T cells to endogenous IL-2, and enhances T cell proliferation. Since activation of TNFRSF25 is T cell receptor dependent, the activity of TNFRSF25 in vivo is specific to T cells that are encountering cognate antigen. At rest, and when there is no underlying autoimmunity, the majority of T cells that regularly encounter cognate antigen are FoxP3+ regulatory T cells. Stimulation of TNFRSF25, in the absence of any other exogenous signals, stimulates highly specific proliferation of FoxP3+ regulatory T cells from a baseline of 8-10% of all CD4+ T cells to 35-40% of all CD4+ T cells, within five days (Schreiber et al., *J Clin Invest* 120(10):3629-3640, 2010). Therapeutic agonists of TNFRSF25 can be used to stimulate Treg expansion, which can reduce inflammation in experimental models of asthma, allogeneic solid organ transplantation, and ocular keratitis (Schreiber et al., supra; Reddy et al., *J Virol* 86(19):10606-10620, 2012; and Wolf et al., *Transplantation* 94(6):569-574, 2012). Similarly, because TNFRSF25 activation is antigen dependent, costimulation of TNFRSF25 together with an autoantigen or with a vaccine antigen can lead to exacerbation of immunopathology or enhanced vaccine-stimulated immunity, respectively (Schreiber et al., *J Immunol* 189(7):3311-3318, 2010).

SUMMARY

This document is based, at least in part, on the development of antibodies targeted to particular epitopes within TNFSF25. In some embodiments, the antibodies can cross-react between species. For example, in some embodiments, the present document provides antibodies that can bind to rodent and human TNFRSF25 polypeptides with $K_d$ values that are within 100-fold (e.g., within 10-fold) of each other. In some cases, the antibodies described herein are capable of eliciting a signaling event that is consistent with the signaling activity of TL1A (e.g., rodent or human TL1A) binding to TNFRSF25. In some embodiments, the antibodies are capable of binding to an epitope in the region of amino acids C48-L71 of human TNFRSF25. For example, the antibodies can bind specifically to an epitope in the region of amino acids P64-T69.

This document also is based, at least in part, on the development of affinity matured antibodies targeted to TNFRSF25. The affinity matured antibodies can have increased affinity for TNFRSFS25, as compared to the parental anti-TNFRSF25 antibody, or the affinity matured antibodies can have increased activity as compared to the parental anti-TNFRSF25 antibody, or the affinity matured antibodies can have both increased TNFRSF25 affinity and increased activity, as compared to the parental anti-TNFRSF25 antibody.

Thus, in a first aspect, this document features an anti-TNFRSF25 antibody or antigen binding fragment thereof. The antibody or antibody fragment can include (i) a heavy chain variable region containing heavy chain CDR1, CDR2, and CDR3 sequences, where the heavy chain CDR1 sequence is GFTFSNHDLN (SEQ ID NO:12), the heavy chain CDR2 sequence is YISSASGLISYADAVRG (SEQ ID NO:14); and the heavy chain CDR3 sequence is DPAYTG-LYALDF (SEQ ID NO:26); and (ii) a light chain variable region containing light chain CDR1, CDR2, and CDR3 sequences, wherein the light chain CDR1 sequence is TLS-SELSWYTIV (SEQ ID NO:25), the light chain CDR2 sequence is LKSDGSHSKGD (SEQ ID NO:21), and the light chain CDR3 sequence is CGAGYTLAGQYGWV (SEQ ID NO:23).

The antibody or antibody fragment can include (i) a heavy chain variable region containing heavy chain CDR1, CDR2, and CDR3 sequences, where the heavy chain CDR1 sequence is GFTFSNHDLN (SEQ ID NO:12), the heavy chain CDR2 sequence is YISSASGLISYADAVRG (SEQ ID NO:14); and the heavy chain CDR3 sequence is DPPYS-GLYALDF (SEQ ID NO:16); and (ii) a light chain variable region containing light chain CDR1, CDR2, and CDR3 sequences, wherein the light chain CDR1 sequence is TLS-SELSWYTIV (SEQ ID NO:25), the light chain CDR2 sequence is LKSDGSHSKGD (SEQ ID NO:21), and the light chain CDR3 sequence is CGAGYTLAGQYGWV (SEQ ID NO:23).

The antibody or antibody fragment can include (i) a heavy chain variable region comprising heavy chain CDR1, CDR2, and CDR3 sequences, wherein the heavy chain CDR1 sequence is GFTFSNHDLN (SEQ ID NO:12), the heavy chain CDR2 sequence is YISSASGLISYADAVRG (SEQ ID NO:14); and the heavy chain CDR3 sequence is DPAYTG-LYALDF (SEQ ID NO:26); and (ii) a light chain variable region comprising light chain CDR1, CDR2, and CDR3 sequences, wherein the light chain CDR1 sequence is TLS-SELSGFTIV (SEQ ID NO:27), the light chain CDR2 sequence is LKSDGSHSKGD (SEQ ID NO:21), and the light chain CDR3 sequence is CGAGYTLANQYGWV (SEQ ID NO:28).

The antibody or antigen binding fragment can further include variable region framework (FW) sequences juxtaposed between the CDRs according to the formula (FW1)-

(CDR1)-(FW2)-(CDR2)-(FW3)-(CDR3)-(FW4), where the variable region FW sequences in the heavy chain variable region are heavy chain variable region FW sequences, and wherein the variable region FW sequences in the light chain variable region are light chain variable region FW sequences. The variable region FW sequences can be human. The antibody or antigen binding fragment can further contain human heavy chain and light chain constant regions. The constant regions can be selected from the group consisting of human IgG1, IgG2, IgG3, and IgG4. The constant regions are IgG1 or IgG4. Tumor cell apoptosis in a subject can be increased following administration of the antibody or antigen binding fragment to the subject at a dose of about 0.1 mg/kg to about 50 mg/kg.

In another aspect, this document features a pharmaceutical composition containing a pharmaceutically acceptable carrier and an antibody or antigen binding fragment as disclosed herein.

In another aspect, this document features an article of manufacture containing the above pharmaceutical composition, and at least one additional agent for treating cancer. The at least one additional agent can be an agent that targets CTLA-4, PD-1, PD-L1, LAG-3, Tim-3, TNFRSF4, TNFRSF9, TNFRSF18, CD27, CD39, CD47, CD73, or CD278, or can be an A2A receptor antagonist or a TGF-beta antagonist. The at least one additional agent can be one or more of a B7 family costimulatory molecule, a TNF receptor superfamily costimulatory molecule, a vaccine composition, or a chemotherapeutic agent. The at least one additional agent can include chimeric antigen receptor-transfected T cells or expanded tumor infiltrating lymphocytes for use in an adoptive T cell therapy in vitro or in a subject. The at least one additional agent can be used during the in vitro manufacturing process of an autologous T cell therapy.

In yet another aspect, this document features a method for treating a tumor in a subject, where the method includes administering to the subject an amount of the composition described herein that is effective to induce apoptosis of TNFRSF25-expressing tumor cells in the tumor.

This document also features a method for stimulating proliferation of CD8+ T cells in a subject, where the method includes administering to the subject a therapeutically effective amount of a composition as described herein. The proliferation of CD8+ T cells can be increased by at least about 20% as compared to the baseline level of proliferation prior to the administering, as determined by flow cytometry analysis of antigen specific CD8+ T cells.

In addition, this document features a method of eliciting an immune response in a subject, where the method includes administering to the subject a therapeutically effective amount of a composition as described herein.

This document also features a method for stimulating proliferation of CD4+FoxP3+ regulatory T cells in a subject, where the method includes administering to the subject a therapeutically effective amount of a composition as described herein.

In another aspect, this document features an isolated monoclonal antibody, or an Fab fragment thereof, that specifically binds to human TNFRSF25, wherein the antibody or Fab fragment thereof, upon binding to TNFRSF25, elicits a signaling event that is consistent with a signaling even elicited by TL1A binding to TNFRSF25, and wherein the antibody binds to an epitope in the region of amino acids C48-L71 of human TNFRSF25. The antibody or fragment can bind to an epitope containing at least one of the following residues of TNFRSF25: C48, R49, G50, C51, P52, A53, G54, H55, Y56, L57, K58, A59, P60, C61, T62, E63, P64, C65, G66, N67, S68, T69, C70, or L71 of SEQ ID NO:1. Binding of the antibody or fragment to TNFRSF25 can block binding of TL1A to TNFRSF25. The antibody can be a humanized antibody or a human antibody. The antibody can be an IgG antibody of any subtype. The antibody or fragment can be capable of binding to mouse TNFRSF25, non-human primate TNFRSF25, and human TNFRSF25 with $K_d$ values within 100-fold of the other.

In another aspect, this document features an isolated monoclonal antibody, or an Fab fragment thereof, that specifically binds to human TNFRSF25, wherein the antibody or Fab fragment thereof, upon binding to TNFRSF25, elicits a signaling event that is characteristic of a signaling even elicited by TL1A binding to TNFRSF25, and wherein the antibody binds to an epitope in the region of amino acids P64-T69 of human TNFRSF25. The antibody or fragment can bind to an epitope containing at least one of the following residues of TNFRSF25: P64, C65, G66, N67, S68, or T69 of SEQ ID NO:1. Binding of the antibody or fragment to TNFRSF25 can block binding of TL1A to TNFRSF25. The antibody can be a humanized antibody or a human antibody. The antibody can be an IgG antibody of any subtype. The antibody or fragment can be capable of binding to mouse TNFRSF25, non-human primate TNFRSF25, and human TNFRSF25 with $K_d$ values within 100-fold of the other.

In another aspect, this document features an isolated monoclonal antibody, or an Fab fragment thereof, that specifically binds to human TNFRSF25, wherein the antibody binds to an epitope having a sequence at least 80% identical to the sequence set forth in C48-L71 of SEQ ID NO:1. In some embodiments, the antibody can bind to an epitope having a sequence at least 90% identical to the sequence set forth in C48-L71 of SEQ ID NO:1, or to an epitope having a sequence at least 95%, at least 98%, or at least 99% identical to the sequence set forth in C48-L71 of SEQ ID NO:1.

In yet another aspect, this document features an isolated monoclonal antibody, or an Fab fragment thereof, that specifically binds to human TNFRSF25, wherein the antibody binds to an epitope having a sequence at least 85%, at least 90%, or at least 95% identical to the sequence set forth in P64-T69 of SEQ ID NO:1.

This document also features an isolated monoclonal antibody, or an Fab fragment thereof, that specifically binds to human TNFRSF25, wherein the antibody binds to an epitope having the sequence set forth in C48-L71 of SEQ ID NO:1, but with four or fewer amino acid substitutions. In some embodiments, the antibody can bind to an epitope having the sequence set forth in C48-L71 of SEQ ID NO:1, but with three or fewer amino acid substitutions, with two or fewer amino acid substitutions, or with one amino acid substitution.

In another aspect, this document features an isolated monoclonal antibody, or an Fab fragment thereof, that specifically binds to human TNFRSF25, wherein the antibody binds to an epitope having the sequence set forth in P64-T69 of SEQ ID NO:1, but with one amino acid substitution.

In still another aspect, this document features a method for inhibiting tumor growth in a mammal. The method can include administering to the mammal a composition containing a pharmaceutically acceptable carrier and a monoclonal antibody, or an Fab fragment thereof, that binds specifically to human TNFRSF25, wherein the antibody or Fab fragment thereof is capable of mimicking a signaling event stimulated by TL1A binding to TNFRSF25, and wherein the antibody binds to an epitope in the region of amino acids C48-L71 of human TNFRSF25. The antibody or fragment can bind to an epitope containing at least one of the following residues of TNFRSF25: C48, R49, G50, C51, P52, A53, G54, H55, Y56, L57, K58, A59, P60, C61, T62, E63, P64, C65, G66, N67, S68, T69, C70, or L71 of SEQ ID NO:1. The antibody or fragment can bind to an epitope containing at least one of the following residues of TNFRSF25: P64, C65, G66, N67, S68, or T69 of SEQ ID NO:1. Binding of the antibody or fragment to TNFRSF25 can block binding of TL1A to TNFRSF25. The antibody can be a humanized antibody or a human antibody. The antibody can be an IgG antibody of any subtype. The antibody or fragment can be capable of binding to mouse TNFRSF25, non-human primate TNFRSF25, and human TNFRSF25 with $K_d$ values within 100-fold of the other.

In another aspect, this document features a pharmaceutical composition containing a pharmaceutically acceptable carrier and an isolated monoclonal antibody or Fab fragment as described herein. In addition, this document features the use of the pharmaceutical composition for treating cancer, infectious disease, or tissue graft in a patient.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is an amino acid sequence alignment of human TNFRSF25 (SEQ ID NO:2) with human TNFR1 (SEQ ID NO:3) and human Fas (SEQ ID NO:4), with which TNFRSF25 shares some homology. Sequence numbering starts at the N-terminus of the predicted mature protein. Locations of cysteine-rich regions I-IV, the transmembrane domain (TM), and the death domain (DD) are indicated. Residues that are identical between at least two of the sequences are bolded and underlined.

FIG. 1B shows two representative TNFRSF25 amino acid sequences from human (SEQ ID NOS:1 and 7), and representative TNFRSF25 amino acid sequences from mouse (SEQ ID NO:8), Rhesus Macaque (SEQ ID NO:9), and Cynomolgus Macaque (SEQ ID NO:10).

DETAILED DESCRIPTION

Figure 2:
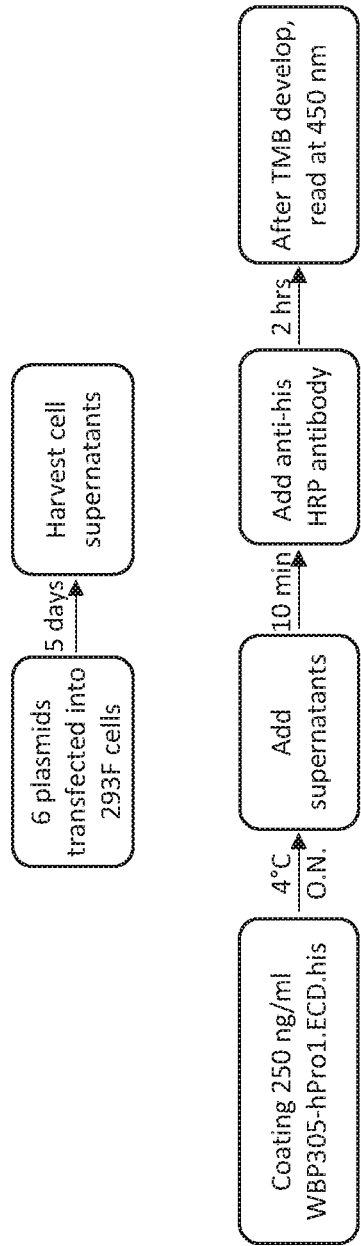
FIG. 2 is a diagram depicting the steps in a method for evaluating expression of various recombinant TNFRSF25 polypeptides.

This document is based, at least in part, on the development of antibodies targeted to particular epitopes within TNFSF25. For example, this document provides antibodies that can bind to epitopes in the region of amino acids C48-L71 of human TNFRSF25. In some embodiments, the antibodies can bind to rodent and human TNFRSF25 polypeptides with $K_d$ values that are within 100-fold (e.g., within 10-fold) of each other, and can be capable of mimicking the signaling activity of rodent or human TL1A binding to TNFRSF25. In some embodiments, the antibodies can bind to an epitope in the region of amino acids P64-T69, which is a conserved region of the polypeptide in placental mammals. Also provided herein are methods for using one or more of the antibodies provided herein, or compositions containing the one or more antibodies, to stimulate proliferation of T cells (e.g., human T cells, murine T cells, or macaque T cells), as well as methods for using the one or more antibodies or compositions to treat human cancer patients (e.g., by administering an amount of an anti-TNFRSF25 antibody that is effective to stimulate proliferation of CD8+ T cells).

This document also provides affinity matured humanized TNFRSF25 specific monoclonal antibodies, and antigen binding fragments of the affinity matured antibodies. Also provided herein are methods for using the affinity matured antibodies to, inter alia, stimulate proliferation of T cells (e.g., human T cells, including naturally-occurring tumor-reactive CD8+ T cells or CD4+FoxP3+ regulatory T cells, as well as murine T cells or macaque T cells), and methods for using affinity matured antibodies in the treatment of cancer and other disease states in which the expansion of T cells can have a beneficial effect (e.g., infectious disease, graft versus host disease, and autoimmune diseases). The methods can include, for example, administering an amount of an affinity matured antibody that is effective to stimulate proliferation of CD8+ T cells or the appropriate population of regulatory T cells.

A partial amino acid sequence for human TNFRSF25 is shown in FIG. 1, aligned with amino acid sequences for human TNFR1 and FAs. A representative full-length amino acid sequence of human TNFRSF25 is:

(SEQ ID NO: 1)
MEQRPRGCAAVAAALLLVLLGARA

QGGTRSPRCDCAGDFHKKIGLFCCRGCPAGHYLKAPCTEPCGNSTCLVCP

QDTFLAWENHHNSECARCQACDEQASQVALENCSAVADTRCGCKPGWFVE

CQVSQCVSSSPFYCQPCLDCGALHRHTRLLCSRRDTDCGTCLPGFYEHGD

GCVSCPTSTLGSCPERCAAVCGWRQMFWVQVLLAGLVVPLLLGATLTYTY

RHCWPHKPLVTADEAGMEALTPPPATHLSPLDSAHTLLAPPDSSEKICTV

QLVGNSWTPGYPETQEALCPQVTWSWDQLPSRALGPAAAPTLSPESPAGS

PAMMLQPGPQLYDVMDAVPARRWKEFVRTLGLREAEIEAVEVEIGRFRDQ

QYEMLKRWRQQQPAGLGAVYAALERMGLDGCVEDLRSRLQRGP

As used herein, the term "antibody" refers to any immunoglobulin or antibody (e.g., human, hamster, feline, mouse, cartilaginous fish, or camelid antibodies), and any derivative or conjugate thereof, that specifically binds to an antigen. A wide variety of antibodies are known by those skilled in the art. Non-limiting examples of antibodies include monoclonal antibodies, polyclonal antibodies, humanized antibodies, multi-specific antibodies (e.g., bi-specific antibodies), single-chain antibodies (e.g., single-domain antibodies, camelid antibodies, and cartilaginous fish antibodies), chimeric antibodies, feline antibodies, and felinized antibodies. Monoclonal antibodies are homogeneous populations of antibodies to a particular epitope of an antigen. Polyclonal antibodies are heterogeneous populations of antibody molecules that are contained in the sera of the immunized animals. The term "antibody" also includes antibody derivatives and conjugates (e.g., an antibody conjugated to a stabilizing protein, a detectable moiety, or a therapeutic agent).

By "isolated" or "purified" with respect to a polypeptide (e.g., an antibody or a fragment thereof), it is meant that the polypeptide is separated to some extent from the cellular components with which would normally be found in nature (e.g., other polypeptides, lipids, carbohydrates, and nucleic acids). In some embodiments, an "isolated" polypeptide is one that is expressed and produced in an environment other than the environment in which the polypeptide would naturally expressed and produced. For example, a plant polypeptide is isolated when expressed and produced in bacteria or fungi. Similarly, a plant polypeptide is isolated when its gene coding sequence is operably linked to a chimeric regulatory element and expressed in a tissue where the polypeptide is not naturally expressed.

An isolated polypeptide can yield a single major band on a non-reducing polyacrylamide gel. An isolated polypeptide can be at least about 75% pure (e.g., at least 80%, 85%, 90%, 95%, 97%, 98%, 99%, or 100% pure). Isolated polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

An "antigen binding fragment" is any portion of a full-length antibody that contains at least one variable domain (e.g., a variable domain of a mammalian (e.g., feline, human, hamster, or mouse) heavy or light chain immunoglobulin, a camelid variable antigen binding domain (VHH), or a cartilaginous fish immunoglobulin new antigen receptor (Ig-NAR) domain) that is capable of specifically binding to an antigen. Non-limiting examples of antibody fragments include Fab, Fab', F(ab')$_2$, and Fv fragments, diabodies, linear antibodies, and multi-specific antibodies formed from antibody fragments. Additional antibody fragments containing at least one camelid VHH domain or at least one cartilaginous fish Ig-NAR domain include mini-bodies, micro-antibodies, subnano-antibodies, and nano-antibodies, and any of the other forms of antibodies described, for example, in U.S. Publication No. 2010/0092470.

An "Fv fragment" is the minimum antibody fragment that contains a complete antigen recognition and binding site. This region consists of a dimer of one heavy chain variable domain and one light chain variable domain in tight, non-covalent association. It is in this configuration that the three complementary determining regions (CDRs) of each variable domain interact to define an antigen binding site on the surface of the VH-VL dimer. The term "complementary determining region" or "CDR" refers to a region within an immunoglobulin (a heavy or light chain immunoglobulin) that forms part of an antigen binding site in an antibody or antigen binding fragment thereof. As is known in the art, heavy chain and light chain immunoglobulins each contain three CDRs, referred to as CDR1, CDR2, and CDR3. In any antibody or antigen binding fragment, the three CDRs from the heavy chain immunoglobulin and the three CDRs from the light chain immunoglobulin together form an antigen binding site in the antibody or antigen binding fragment thereof. The Kabat Database is one system used in the art to number CDR sequences present in a light chain immunoglobulin or a heavy chain immunoglobulin.

Collectively, the six CDR's confer antigen binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain ($C_H1$) of the heavy chain. The "Fab fragment" differs from the "Fab' fragment" by the addition of a few residues at the carboxy terminus of the heavy chain $C_H1$ domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art. For example, F(ab')2 fragments can be produced by pepsin digestion of an antibody molecule, and Fab fragments can be generated by reducing the disulfide bridges of F(ab')2 fragments. In some cases, Fab expression libraries can be constructed. See, for example, Huse et al., Science, 246:1275, 1989. Once produced, antibodies or fragments thereof can be tested for recognition of a TNFRSF25 polypeptide using standard immunoassay methods such as ELISA techniques, radioimmunoassays, and Western blotting. See, *Short Protocols in Molecular Biology*, Chapter 11, Green Publishing Associates and John Wiley & Sons, Ed. Ausubel et al., 1992.

An antibody can be of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

In some embodiments, antibodies as provided herein can be fully human or humanized antibodies. By "human antibody" is meant an antibody that is encoded by a nucleic acid (e.g., a rearranged human immunoglobulin heavy or light chain locus) present in the genome of a human. In some embodiments, a human antibody can be produced in a human cell culture (e.g., feline hybridoma cells). In some embodiments, a human antibody can be produced in a non-human cell (e.g., a mouse or hamster cell line). In some embodiments, a human antibody can be produced in a bacterial or yeast cell.

Human antibodies can avoid certain problems associated with xenogeneic antibodies, such as antibodies that possess murine or rat variable and/or constant regions. For example, because the effector portion is human, it can interact better with other parts of the human immune system, e.g., to destroy target cells more efficiently by complement-dependent cytotoxicity or antibody-dependent cellular cytotoxicity. In addition, the human immune system should not recognize the antibody as foreign. Further, half-life in human circulation will be similar to naturally occurring human antibodies, allowing smaller and less frequent doses to be given. Methods for preparing human antibodies are known in the art.

As used herein, the term "humanized antibody" refers to a human antibody that contains minimal sequence derived from non-human (e.g., mouse, hamster, rat, rabbit, or goat) immunoglobulin. Humanized antibodies generally are chimeric or mutant monoclonal antibodies from mouse, rat, hamster, rabbit or other species, bearing human constant and/or variable region domains or specific changes. In non-limiting examples, humanized antibodies are human antibodies (recipient antibody) in which hypervariable region (HVR) residues of the recipient antibody are replaced by HVR residues from a non-human species (donor) antibody, such as a mouse, rat, rabbit, or goat antibody having the desired specificity, affinity, and capacity. In some embodiments, Fv framework residues of the human immunoglobulin can be replaced by corresponding non-human residues. In some embodiments, humanized antibodies can contain residues that are not found in the recipient antibody or in the donor antibody. Such modifications can be made to refine antibody performance, for example.

In some embodiments, a humanized antibody can contain substantially all of at least one, and typically two, variable domains, in which all or substantially all of the hypervariable loops (CDRs) correspond to those of a non-human immunoglobulin, while all or substantially all of the framework regions are those of a human immunoglobulin sequence. A humanized antibody also can contain at least a portion of an immunoglobulin constant (Fc) region, typically that of a human immunoglobulin.

In some embodiments, a humanized antibody or antigen binding fragment as provided herein can have reduced or minimal effector function (e.g., as compared to corresponding, non-humanized antibody), such that it does not stimulate effector cell action to the same extent that a corresponding non-humanized antibody would.

Techniques for generating humanized antibodies are well known to those of skill in the art. In some embodiments, controlled rearrangement of antibody domains joined through protein disulfide bonds to form new, artificial protein molecules or "chimeric" antibodies can be utilized (Konieczny et al., *Haematologia (Budap.)* 14:95, 1981). Recombinant DNA technology can be used to construct gene fusions between DNA sequences encoding mouse antibody variable light and heavy chain domains and human antibody light and heavy chain constant domains (Morrison et al., *Proc Natl Acad Sci USA* 81:6851, 1984). For example, DNA sequences encoding antigen binding portions or CDRs of murine monoclonal antibodies can be grafted by molecular means into DNA sequences encoding frameworks of human antibody heavy and light chains (Jones et al., *Nature* 321: 522, 1986; and Riechmann et al., *Nature* 332:323, 1988). Expressed recombinant products are called "reshaped" or humanized antibodies, and contain the framework of a human antibody light or heavy chain and antigen recognition portions, CDRs, of a murine monoclonal antibody.

Other methods for designing heavy and light chains and for producing humanized antibodies are described in, for example, U.S. Pat. Nos. 5,530,101; 5,565,332; 5,585,089; 5,639,641; 5,693,761; 5,693,762; and 5,733,743. Yet additional methods for humanizing antibodies are described in U.S. Pat. Nos. 4,816,567; 4,935,496; 5,502,167; 5,558,864; 5,693,493; 5,698,417; 5,705,154; 5,750,078; and 5,770,403, for example.

The term "single-chain antibody" refers to a single polypeptide that contains at least one variable binding domain (e.g., a variable domain of a mammalian heavy or light chain immunoglobulin, a camelid VHH, or a cartilaginous fish (e.g., shark) Ig-NAR domain) that is capable of specifically binding to an antigen. Non-limiting examples of single-chain antibodies include single-domain antibodies.

As used herein, the term "single-domain antibody" refers to a polypeptide that contains one camelid VHH or at least one cartilaginous fish Ig-NAR domain that is capable of specifically binding to an antigen. Non-limiting examples of single-domain antibodies are described, for example, in U.S. Publication No. 2010/0092470.

An antibody or antigen binding fragment thereof "specifically binds" to a particular antigen, e.g., TNFRFS25, when it binds to that antigen in a sample, and does not recognize and bind, or recognizes and binds to a lesser extent, other molecules in the sample. In some embodiments, an antibody or an antigen binding fragment thereof can selectively bind to an epitope with an affinity ($K_d$) equal to or less than, for example, about $1\times10^{-6}$ M (e.g., equal to or less than about $1\times10^{-9}$ M, equal to or less than about $1\times10^{-10}$ M, equal to or less than about $1\times10^{11}$ M, or equal to or less than about $1\times10^{-12}$ M) in phosphate buffered saline. The ability of an antibody or antigen binding fragment to specifically bind a protein epitope can be determined using any of the methods known in the art or those methods described herein (e.g., by Biacore/Surface Plasmon Resonance). This can include, for example, binding to TNFRSF25 on live cells as a method to stimulate caspase activation in live transformed cells, binding to an immobilized target substrate including human TNFRSF25 fusion proteins as detected using an ELISA method, binding to TNFRSF25 on live cells as detected by flow cytometry, or binding to an immobilized substrate by surface plasmon resonance (including ProteOn).

Antibodies having specific binding affinity for TNFRSF25 can be produced using standard methods. For example, a TNFRSF25 polypeptide (e.g., having the sequence set forth in SEQ ID NO:1, SEQ ID NO:2, or a fragment of SEQ ID NO:1 or SEQ ID NO:2 that is at least six to ten amino acids in length) can be recombinantly produced, purified from a biological sample (e.g., a heterologous expression system), or chemically synthesized, and used to immunize host animals, including rabbits, chickens, mice, guinea pigs, or rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a TNFRSF25 polypeptide and standard hybridoma technology. In particular, monoclonal antibodies can be obtained by any technique that provides for the production of antibody molecules by continuous cell lines in culture such as described by Kohler et al. (*Nature* 256:495, 1975), the human B-cell hybridoma technique of Kosbor et al. (*Immunology Today,* 4:72, 1983) or Cote et al. (*Proc. Natl. Acad. Sci. USA,* 80:2026, 1983), and the EBV-hybridoma technique described by Cole et al. (*Monoclonal Antibodies and Cancer Therapy*, Alan R. Liss, Inc., pp. 77-96, 1983). Such antibodies can be of any immunoglobulin class including IgG, IgM, IgE, IgA, IgD, and any subclass thereof. The hybridoma producing the monoclonal antibodies can be cultivated in vitro and in vivo.

In some embodiments, a monoclonal anti-TNFRSF25 antibody as provided herein has a heavy chain variable region containing the amino acid sequence set forth in SEQ ID NO:5, but with one to 24 modifications (e.g., substitutions, additions, or deletions) such that the amino acid sequence is between 80% and 99.5% identical to SEQ ID NO:5. In some embodiments, a monoclonal anti-TNFRSF25 antibody as provided herein has a light chain variable region containing the amino acid sequence set forth in SEQ ID NO:6, but with one to 23 modifications (e.g., substitutions, additions, or deletions) such that the amino acid sequence is between 80% and 99.9% identical to SEQ ID NO:6. The sequences of SEQ ID NO:5 and SEQ ID NO:6 are as follows:

```
                                            (SEQ ID NO: 5)
EVQLVESGGGLSQPGNSLQLSCEASGFTFSNHDLNWVRQAPGKGLEWVAY
ISSASGLISYADAVRGRFTISRDNAKNSLFLQMNNLKSEDTAMYYCARDP
PYSGLYALDFWGQGTQVTVSS (SEQ ID NO: 6)
QPVLTQSPSASASLSGSVKLTCTLSSELSSYTIVWYQQRPDKAPKYVMYL
KSDGSHSKGDGIPDRFSGSSSGAHRYLSISNVQSEDDATYFCGAGYTLAG
QYGWVFGSGTKVTVL
```

Thus, this document provides heavy chain variable region polypeptides containing the amino acid sequence set forth in SEQ ID NO:5, or an antigen binding fragment thereof, but with one to 24 sequence modifications, as well as polypeptides having at least about 80% (e.g., about 85%, about 90%, about 91%, about 92%, about 93%, about 94%, about 95%, about 96%, about 97%, about 98%, or about 99%) amino acid sequence identity to SEQ ID NO:5, or an antigen binding fragment thereof. In some embodiments, a heavy chain variable region polypeptide can contain 24 or less (e.g., 24, 23, 22, 21, 20, 19, 18, 17, 16, 15, 14, 13, 12, 11, ten, nine, eight, seven, six, five, four, three, two, or one) amino acid substitution as compared to SEQ ID NO:5, or an antigen binding fragment thereof.

This document also provides light chain variable region polypeptides containing the amino acid sequence set forth in SEQ ID NO:6, or an antigen binding fragment thereof, but with one to 23 sequence modifications, as well as polypeptides having at least about 80% (e.g., about 85%, about 90%, about 91%, about 92%, about 93%, about 94%, about 95%, about 96%, about 97%, about 98%, or about 99%) amino acid sequence identity to SEQ ID NO:6, or an antigen binding fragment thereof. In some embodiments, a light chain variable region polypeptide can contain 23 or less (e.g., 23, 22, 21, 20, 19, 18, 17, 16, 15, 14, 13, 12, 11, ten, nine, eight, seven, six, five, four, three, two, or one) amino acid substitutions as compared to SEQ ID NO:6, or an antigen binding fragment thereof.

This document also provides antibodies and antigen binding fragments that contain both a heavy chain variable region polypeptide and a light chain variable region polypeptide as disclosed herein. In some embodiments, for example, an antibody or antigen binding fragment can contain both a heavy chain variable region sequence comprising the amino acid sequence set forth in SEQ ID NO:5 with one to 24 amino acid substitutions (e.g., one to five, five to ten, ten to 15, 15 to 20, or 20 to 24 total amino acid substitutions), and a light chain variable region sequence comprising the amino acid sequence of SEQ ID NO:6 with one to 23 amino acid substitutions (e.g., one to five, five to ten, ten to 15, 15 to 20, or 20 to 23 total amino acid substitution). An amino acid substitution refers to the replacement of one amino acid residue with another in a peptide sequence.

In some embodiments, an anti-TNFRSF25 antibody or antigen-binding fragment thereof, as provided herein, can bind to an epitope of TNFRSF25 that has an amino acid sequence with at least 80% identity (e.g., at least 85%, at least 90%, or at least 95% identity) to the sequence set forth in C48-L71 of SEQ ID NO:1. For example, in some cases an antibody or antigen-binding fragment thereof can bind to an epitope of TNFRSF25 that has the sequence set forth in C48-L71 of SEQ ID NO:1, but with four or fewer (e.g., three or fewer, or two or fewer) amino acid substitutions, or with one amino acid substitution.

In some embodiments, an anti-TNFRSF25 antibody or antigen-binding fragment thereof, as provided herein, can bind to an epitope of TNFRSF25 that has an amino acid sequence with at least 85% identity to the sequence set forth in P64-T69 of SEQ ID NO:1. For example, in some cases an antibody or antigen-binding fragment thereof can bind to an epitope of TNFRSF25 that has the sequence set forth in P64-T69 of SEQ ID NO:1, but with one amino acid substitution.

As described herein, a humanized monoclonal antibody against TNFRSF25, generated as described elsewhere (see, WO 2016/081455) was used in affinity maturation studies, leading to the identification of several heavy and light chain variable region CDR modifications that appeared to be associated with increased affinity and/or activity. Interestingly, however, and as discussed in Example 3 herein, the clones demonstrating the greatest binding affinity for TNFRSF25 were not always the clones that had the greatest activity over the parent antibody. For example, a clone identified herein as "M5" showed improved agonistic activity as determined by a caspase-3 release assay, but surprisingly, its binding to a TNFRSF25-Fc fusion protein was significantly weaker than most of the other clones identified by combinatorial library screening. An exception to this finding was a clone identified as "M4," which exhibited both improved binding to TNFRSF25-Fc and improved agonistic activity as compared to the parent antibody.

Thus, in some cases, the antibodies provided herein can have increased binding affinity for TNFRSF25, increased agonistic activity (e.g., as determined by caspase-3 assay), or both increased affinity and activity, as compared to the parental humanized 4C12 antibody. By "increased" affinity or activity is meant an increase of at least 5% (e.g., at least 10%, 20%, 30%, 40%, 50%, 60%, 70%, 80%, 90%, 100%, or more than 100%) as compared to the affinity or agonist activity of humanized 4C12. Sequences of the variable regions of the 4C12 heavy and light chains are set forth herein in SEQ ID NOS:5 and 6, respectively. The agonistic activity of an antibody can be assessed using, for example, a caspase-3 assay as described herein, or a TNFRSF25 receptor signaling assay as described elsewhere (see, e.g., Bu et al., Bone 33(5):760-770, 2003).

In some embodiments, therefore, this document provides heavy chain variable region polypeptides containing the CDR1 sequence set forth in SEQ ID NO:12, the CDR2 sequence set forth in SEQ ID NO:14, and a CDR3 sequence as set forth in any of SEQ ID NOS:16, 26, and 32. The polypeptide also can include variable region heavy chain framework (FW) sequences juxtaposed between the CDRs, according to the formula (FW1)-(CDR1)-(FW2)-(CDR2)-(FW3)-(CDR3)-(FW4), for example. In some embodiments, the FW sequences can be human sequences. In some embodiments, a heavy chain variable region polypeptide can include the FW1 sequence set forth in SEQ ID NO:11, the FW2 sequence set forth in SEQ ID NO:13, the FW3 sequence set forth in SEQ ID NO:15, and the FW4 sequence set forth in SEQ ID NO:17.

This document also provides light chain variable region polypeptides containing a CDR1 sequence as set forth in any of SEQ ID NOS:25, 27, and 29, the CDR2 sequence set forth in SEQ ID NO:21, and a CDR3 sequence as set forth in any of SEQ ID NOS:23, 28, and 30. The polypeptide also can include variable region light chain FW juxtaposed between the CDRs, according to the formula (FW1)-(CDR1)-(FW2)-(CDR2)-(FW3)-(CDR3)-(FW4). In some cases, the FW sequences can be human sequences. In some embodiments, a light chain variable region polypeptide can include the FW1 sequence set forth in SEQ ID NO:18, the FW2 sequence set forth in SEQ ID NO:20, the FW3 sequence set forth in SEQ ID NO:22, and the FW4 sequence set forth in SEQ ID NO:24.

This document also provides antibodies and antigen binding fragments that contain both a heavy chain variable region polypeptide and a light chain variable region polypeptide as disclosed herein. In some embodiments, for example, an antibody or antigen binding fragment can contain both a heavy chain variable region sequence having heavy chain CDR sequences as disclosed herein, and a light chain variable region sequence having light chain CDR sequences as disclosed herein. In some cases, the antibody is not a 4C12 antibody, such that it does not contain heavy chain variable region CDRS as set forth in SEQ ID NOS:12, 14, and 16, and does not contain light chain variable region CDRs as set forth in SEQ ID NOS:19, 21, and 23.

In some embodiments, amino acid substitutions can be made by selecting conservative substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of conservative substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. In some embodiments, an amino acid substitution can be non-conservative, such that a member of one of the amino acid classes described above is exchanged for a member of another class.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, an amino acid sequence that has 110 matches when aligned with the sequence set forth in SEQ ID NO:1 is 90.9 percent identical to the sequence set forth in SEQ ID NO:1 (i.e., 110÷121×100=90.9). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

In addition, this document also provides pharmaceutical compositions that contain an antibody or antigen binding fragment as described herein, in combination with a pharmaceutically acceptable carrier. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a mammal, such as a human, non-human primate, dog, cat, sheep, pig, horse, cow, mouse, rat, or rabbit), which is nontoxic to the cell or subject being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al. *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can contain sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing an antibody or antigen binding fragment as provided herein can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Any appropriate method can be used to administer an antibody or antigen binding fragment as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing an antibody or antigen binding fragment as described herein can be administered prior to, after, or in lieu of surgical resection of a tumor.

A composition containing an anti-TNFRSF25 antibody or antigen binding fragment can be administered to a mammal in any appropriate amount, at any appropriate frequency, and for any appropriate duration effective to achieve a desired outcome. For example, an anti-TNFRSF25 antibody or antigen binding fragment can be administered to a subject in an amount effective to stimulate proliferation of T cells in vitro or in vivo (e.g., human, murine, hamster, or macaque T cells, including CD8+ T cells and/or CD4+FoxP3+ regulatory T cells), to stimulate apoptosis of tumor cells that express TNFRSF25, to reduce tumor size, or to increase progression-free survival of a cancer patient. In some embodiments, an anti-TNFRSF25 antibody or antigen binding fragment can be administered at a dosage of about 0.1 mg/kg to about 10 mg/kg (e.g., about 0.1 mg/kg to about 1 mg/kg, about 1 mg/kg to about 5 mg/kg, or about 5 mg/kg to about 10 mg/kg), and can be administered once every one to three weeks (e.g., every week, every 10 days, every two weeks, or every three weeks).

Administration to a subject of an antibody or antigen binding fragment as provided herein can result in increased numbers of T cells (e.g., naturally-occurring tumor-reactive CD8+ T cells or CD4+FoxP3+ regulatory T cells) that can exert anti-cancer effects against cancer cells present within the mammal. Thus, this document also provides methods for stimulating proliferation of T cells in a subject, by administering to the subject an antibody, antigen-binding fragment, or composition as disclosed herein. In some cases, a composition containing an anti-TNFRSF25 antibody or antigen binding fragment as described herein can be administered to a subject in an amount effective to increase proliferation of T cells (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the "baseline" level of T cell proliferation in the subject prior to administration of the composition, or as compared to the level of T cell proliferation in a control subject or population of subjects to whom the composition was not administered. The T cells can be, for example, CD8+ T cells, or CD4+FoxP3+ regulatory T cells. Any suitable method can be used to determine whether or not the level of T cell proliferation is increased in the subject. Such methods can include, without limitation, flow cytometry analysis of antigen specific T cells (e.g., flow cytometry analysis of the proportion of antigen specific CD8+ T cells as a fraction of the total CD8+ T cell pool), analysis of cell proliferation markers (e.g., expression of Ki67) in CD8+ T cells, increased counts of CD8+ T cells, or increased proportions of individual TCR sequences of a particular clone of CD8+ T cells.

This document also provides methods for promoting apoptosis of TNFRSF25-expressing tumor cells in a subject, by treating the subject with an antibody, antigen-binding fragment, or composition as described herein. In some cases, a composition containing an antibody or antigen binding fragment as provided herein can be administered to a subject (e.g., a cancer patient) in an amount effective to increase apoptosis of TNFRSF25-expressing tumor cells (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the "baseline" level of tumor cell apoptosis in the subject prior to administration of the composition, or as compared to the level of tumor cell apoptosis in a control subject or population of subjects to whom the composition was not administered. Any suitable method can be used to determine whether or not the level of tumor cell apoptosis is increased in the subject. This can include, for example, radiologic techniques such as CT or MM, with or without contrast that indicates the presence of a necrotic or apoptotic tumor, biopsy of a tumor sample indicating increased tumor cell death, caspase induction within tumor cells, elimination of detectable tumor lesions by radiologic, or surgical or physical examination.

Methods for treating a subject (e.g., a human patient) with cancer, including solid tumors and leukemias/lymphomas) also are provided herein. In some cases, a composition containing an antibody or antigen binding fragment as described herein can be administered to a subject having cancer in an amount effective to reduce the progression rate of the cancer (e.g., by at least about 10 percent, about 20 percent, about 25 percent, about 50 percent, about 60 percent, about 70 percent, about 75 percent, about 80 percent, about 90 percent, or more than 90 percent), as compared to the rate of cancer progression in the subject prior to administration of the composition, or as compared to the rate of cancer progression in a control subject or population of subjects to whom the composition was not administered. In some embodiments, the progression rate can be reduced such that no additional cancer progression is detected. Any appropriate method can be used to determine whether or not the progression rate of cancer is reduced. For skin cancer (e.g., melanoma), for example, the progression rate can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate has been reduced.

A composition containing an antibody or antigen binding fragment as described herein also can be administered to a subject having cancer under conditions where progression-free survival is increased (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the median progression-free survival of corresponding subjects having untreated cancer or the median progression-free survival of corresponding subjects having cancer and treated with other therapies (e.g., chemotherapeutic agents alone). Progression-free survival can be measured over any length of time (e.g., one month, two months, three months, four months, five months, six months, or longer).

An effective amount of a composition containing a molecule as provided herein can be any amount that has a desired defect (e.g., stimulates proliferation of CD8+ T cells, stimulates apoptosis of TNFRSF25-expressing tumor cells, stimulates or elicits an immune response in a subject, reduces tumor size, reduces the progression rate of cancer, increases progression-free survival of a cancer patient, or increases the median time to progression without producing significant toxicity). Optimum dosages can vary depending on the relative potency of individual polypeptides (e.g., antibodies and antigen binding fragments), and can generally be estimated based on $EC_{50}$ found to be effective in in vitro and in vivo animal models. Typically, dosage is from 0.01 µg to 100 g per kg of body weight. For example, an effective amount of an antibody or antigen binding fragment can be from about 0.1 mg/kg to about 50 mg/kg (e.g., about 0.4 mg/kg, about 2 mg/kg, about 5 mg/kg, about 10 mg/kg, about 20 mg/kg, about 30 mg/kg, about 40 mg/kg, or about 50 mg/kg), or any range there between, such as about 0.1 mg/kg to about 10 mg/kg, about 0.4 mg/kg to about 20 mg/kg, about 2 mg/kg to about 30 mg/kg, or about 5 mg/kg to about 40 mg/kg. If a particular subject fails to respond to a particular amount, then the amount of the antibody or antigen binding fragment can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that, for example, stimulates proliferation of CD8+ T cells, stimulates apoptosis of TNFRSF25-expressing tumor cells, reduces tumor size, reduces the progression rate of cancer, increases progression-free survival of a cancer patient, or increases the median time to progression without producing significant toxicity. For example, the frequency of administration can be once or more daily, biweekly, weekly, monthly, or even less. The frequency of administration can remain constant or can be variable during the duration of treatment. A course of treatment can include rest periods. For example, a composition containing an antibody or antigen binding fragment as provided herein can be administered over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that stimulates proliferation of CD8+ T cells, stimulates apoptosis of TNFRSF25-expressing tumor cells, reduces tumor size, reduces the progression rate of cancer, increases progression-free survival of a cancer patient, or increases the median time to progression without producing significant toxicity. Thus, an effective duration can vary from several days to several weeks, months, or years. In general, the effective duration for the treatment of cancer can range in duration from several weeks to several months. In some cases, an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the cancer.

After administering a composition as provided herein to a cancer patient, the patient can be monitored to determine whether or not the cancer was treated. For example, a subject can be assessed after treatment to determine whether or not the progression rate of the cancer has been reduced (e.g., stopped). Any method, including those that are standard in the art, can be used to assess progression and survival rates.

A method for using an antibody or antigen binding fragment as provided herein can be combined with known methods of treatment for cancer, for example, either as combined or additional treatment steps, or as additional components of a therapeutic formulation. For example, enhancing a host's immune function can be useful to combat tumors. Methods can include, without limitation, APC enhancement, such as by injection into a tumor of DNA encoding foreign MEW antigens (including tumor antigens, mutation derived antigens, or other antigens), or transfecting biopsied tumor cells with genes that increase the probability of immune antigen recognition (e.g., immune stimulatory cytokines, GM-CSF, or co-stimulatory molecules B7.1, B7.2) of the tumor. Other methods can include, for example, solubilization of specific tumor antigens into depot or sustained release preparations, transfection of allogeneic tumor cells with adjuvant proteins or antigen carrier proteins, transfection of allogeneic tumor cells with immune stimulatory proteins such as alpha galactosylceramide, incorporation of specific tumor antigens into virus-derived vaccine regimens, incorporation of specific tumor antigens into *Listeria* derived vaccine regimens, adoptive cellular immunotherapy (including chimeric antigen receptor transfected T cells), or treatment with activated tumor-specific T-cells (including ex vivo expanded tumor infiltrating lymphocytes). Adoptive cellular immunotherapy can include isolating tumor-infiltrating host T-lymphocytes and expanding the population in vitro (e.g., by stimulation with IL-2). The T-cells then can be re-administered to the host. Other treatments that can be used in combination with an antibody or antigen-binding fragment as provided herein include, for example, radiation therapy, chemotherapy, hormonal therapy, and the use of angiogenesis inhibitors. Further combination partners that may be useful include checkpoint inhibitors (e.g., anti-PD1/L1, anti-CTLA-4, anti-LAG3, anti-B7-H3, anti-B7-H4, anti-TIM3, anti-TIGIT, anti-CD47, anti-TMIGD2, anti-BTLA, anti-CEACAM, or anti-GARP), other costimulatory antibodies (e.g., anti-OX40, anti-ICOS, anti-CD137, anti-GITR, or anti-CD40), cancer vaccines (e.g., virus based vaccines, peptide vaccines, whole-cell vaccines, or RNA based vaccines), and targeted agents [e.g., HERCEPTIN® (trastuzumab), TARCEVA® (erlotinib), AVASTIN® (bevacizumab), or IMBRUVICA® (ibrutinib)].

Thus, in some embodiments, an anti-TNFRSF25 antibody or antigen binding fragment can be used in combination with one or more additional monoclonal antibodies that inhibit binding of PD-L1 to PD-1, inhibit binding of CTLA-4 to CD80 or CD86, or activate signaling via the TNFRSF4, TNFRSF9, or TNFRSF18 pathways, for example. This also can include administration with another antibody, fusion protein, or small molecule that binds a specific target on a tumor cell (e.g., combinations with monoclonal antibodies that bind targets such as CD20, Her2, EGFRvIII, DR4, DR5, VEGF, CD39, and CD73). An anti-TNFRSF25 antibody or antigen binding fragment also can be used in combination with a cancer vaccine approach to enhance the activation of tumor antigen specific T cells in a cancer patient. In addition, an anti-TNFRSF25 antibody or antigen binding fragment can be used after administration of autologous or allogeneic T or NK cells engineered to express a chimeric T cell receptor that recognizes a specific tumor antigen. Further, an anti-TNFRSF25 antibody or antigen binding fragment can be used in combination with specific chemotherapy or radiation therapy strategies as a method to expand tumor specific T cells and enhance the activity of either approach as a monotherapy in a cancer patient.

When one or more conventional therapies are combined with treatment using an anti-TNFRSF25 antibody or antigen binding fragment as provided herein for treating cancer, for example, the conventional therapy(ies) can be administered prior to, subsequent to, or simultaneously with administration of the anti-TNFRSF25 antibody or antigen binding fragment. For example, a PD-1 blocking antibody can be administered to a patient prior to administration of a TNFRSF25 agonist antibody. Such a regimen can be cycled over a period of weeks, months, or years, for example. Alternatively, a PD-1 blocking antibody can be administered at the same time or after administration of a TNFRSF25 agonist antibody. Such a regimen also can be cycled over a period of weeks, months, or years. In some embodiments, combination therapies that are repeatedly administered over a period of time can include two or more of the above administration strategies.

In some embodiments, an anti-TNFRSF25 antibody or antigen binding fragment as provided herein can be used during an in vitro assay or manufacturing process as a method for stimulating proliferation of tumor infiltrating lymphocytes isolated from a cancer patient, or to stimulate proliferation of chimeric antigen receptor expressing T cells being expanded in vitro and intended for subsequent infusion for the treatment of a cancer patient.

Also provided herein are articles of manufacture containing an antibody or antigen binding fragment as described herein, or a pharmaceutical composition containing the antibody or antigen binding fragment. The antibody or pharmaceutical composition can be within a container (e.g., a bottle, vial, or syringe). The article of manufacture also can include a label with directions for reconstituting and/or using the antibody, antigen binding fragment, or composition. In some embodiments, an article of manufacture can include one or more additional items (e.g., one or more buffers, diluents, filters, needles, syringes, and/or package inserts with further instructions for use). An article of manufacture also can include at least one additional agent for treating cancer. For example, an article of manufacture as provided herein can contain an agent that targets CTLA-4, PD-1, PD-L1, LAG-3, Tim-3, TNFRSF4, TNFRSF9, TNFRSF18, CD27, CD39, CD47, CD73, or CD278. In some embodiments, an article of manufacture can contain an A2A receptor antagonist or a TGF-beta antagonist. In some embodiments, an article of manufacture can include a B7 family costimulatory molecule (e.g., CD28 or CD278) or a TNF receptor superfamily costimulatory molecule (e.g., TNFRSF4, TNFRSF9, or TNFRSF18), a chemotherapeutic agent, or an anti-tumor vaccine composition.

The invention will be further described in the following examples, which do not limit the scope of the invention described in the claims.

EXAMPLES

Example 1—Epitope Mapping

Several TNFRSF25 expression constructs were prepared. These included either the entire extracellular domain (ECD) extending from the Gln at position 25 (Q25) to the Phe at position 201 (F201), or a soluble splice variant extending from Q25 to the Thr at position 181 (T181). The constructs also included various tags, including 6His, hFc-6His, and mFc-His. Six constructs (TABLE 1) were transfected into 293F cells, and their expression levels were measured as depicted in FIG. 2.

TABLE 1

| Sample | Protein |
|---|---|
| Whis | W381-hPro1.ECD-W.His |
| WmFchis | W381-hPro1.ECD-W.mFcHis |
| WhFchis | W381-hPro1.ECD-W.hFcHis |
| Mhis | W381-hPro1.ECD-M.His |
| MmFchis | W381-hPro1.ECD-M.mFcHis |
| MhFchis | W381-hPro1.ECD-M.hFcHis |
| NC | Negative Control (plasfect) |

W = extracellular domain (QGGT . . . GWRQMF)
M = soluble splice variant (QGGT . . . SCPT)

Figure 3:
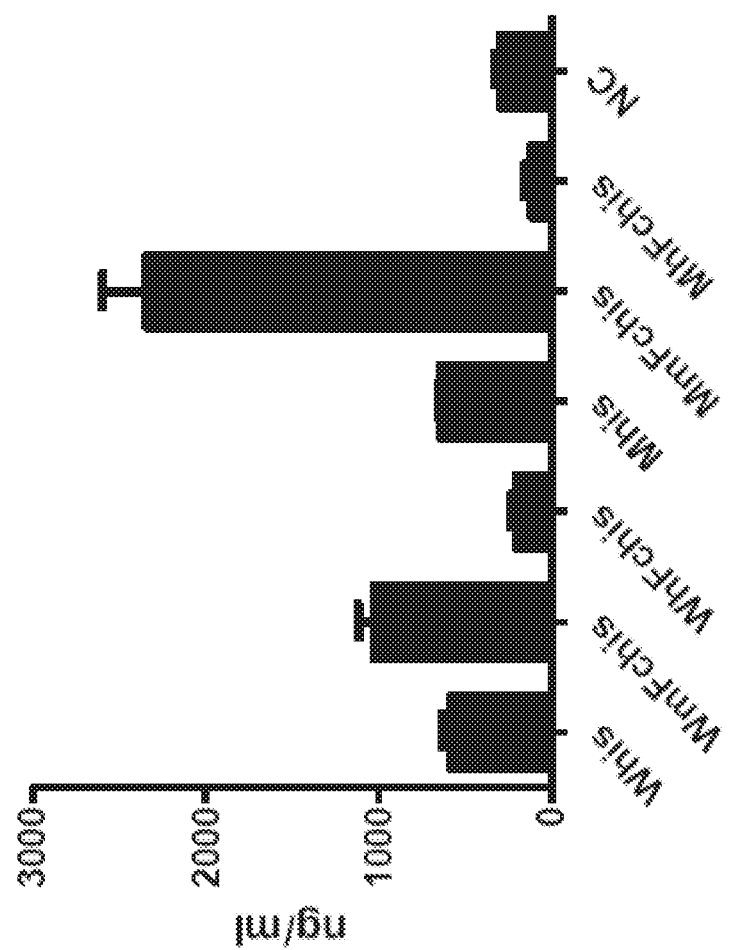
FIG. 3 is a graph plotting expression levels for six recombinant TNFRSF25 polypeptides.

Of the constructs tested, W381-hPro1.ECD-M.mFcHis demonstrated the highest expression (FIG. 3). This version of TNFRSF25 therefore was chosen as the backbone for alanine scanning-based epitope mapping.

Seventy-three alanine mutants were generated, and their expression was measured as described above. The mutants were divided into five groups based on their expression levels (TABLES 2A and 2B), and were used for binding activity analysis.

TABLE 2A

| Expression level | # of Mutants |
|---|---|
| >1500 | 27 |
| 1000-1500 | 14 |
| 600-1000 | 17 |
| 300-600 | 14 |
| <300 | 1 |
| Total | 73 |

Figure 4:
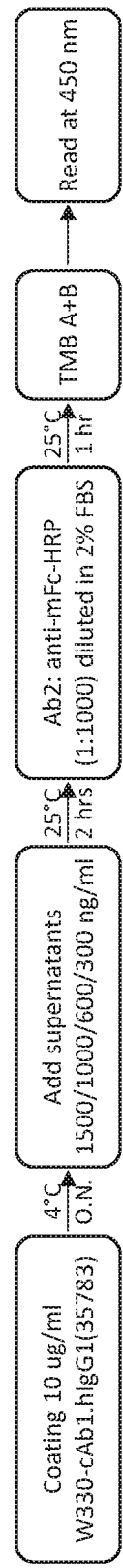
FIG. 4 is a diagram depicting the steps in a method for assessing the binding of a chimeric anti-TNFRSF25 antibody to recombinant TNFRSF25 polypeptides.
Figure 5:
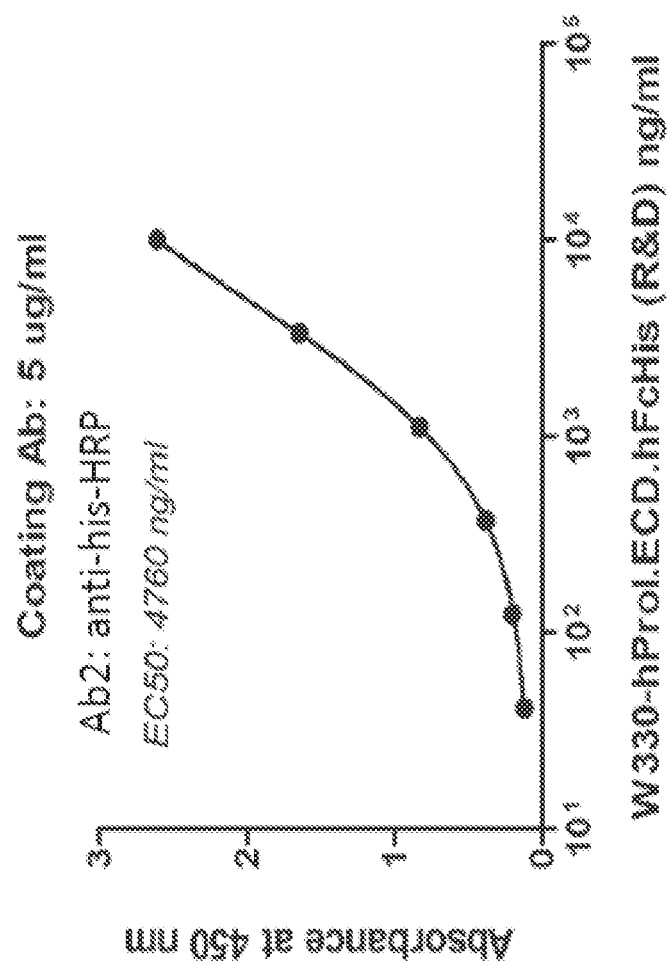
FIG. 5 is a graph plotting the binding of increasing amounts of a recombinant TNFRSF25 polypeptide to a chimeric anti-TNFRSF25 antibody.
Figure 6:
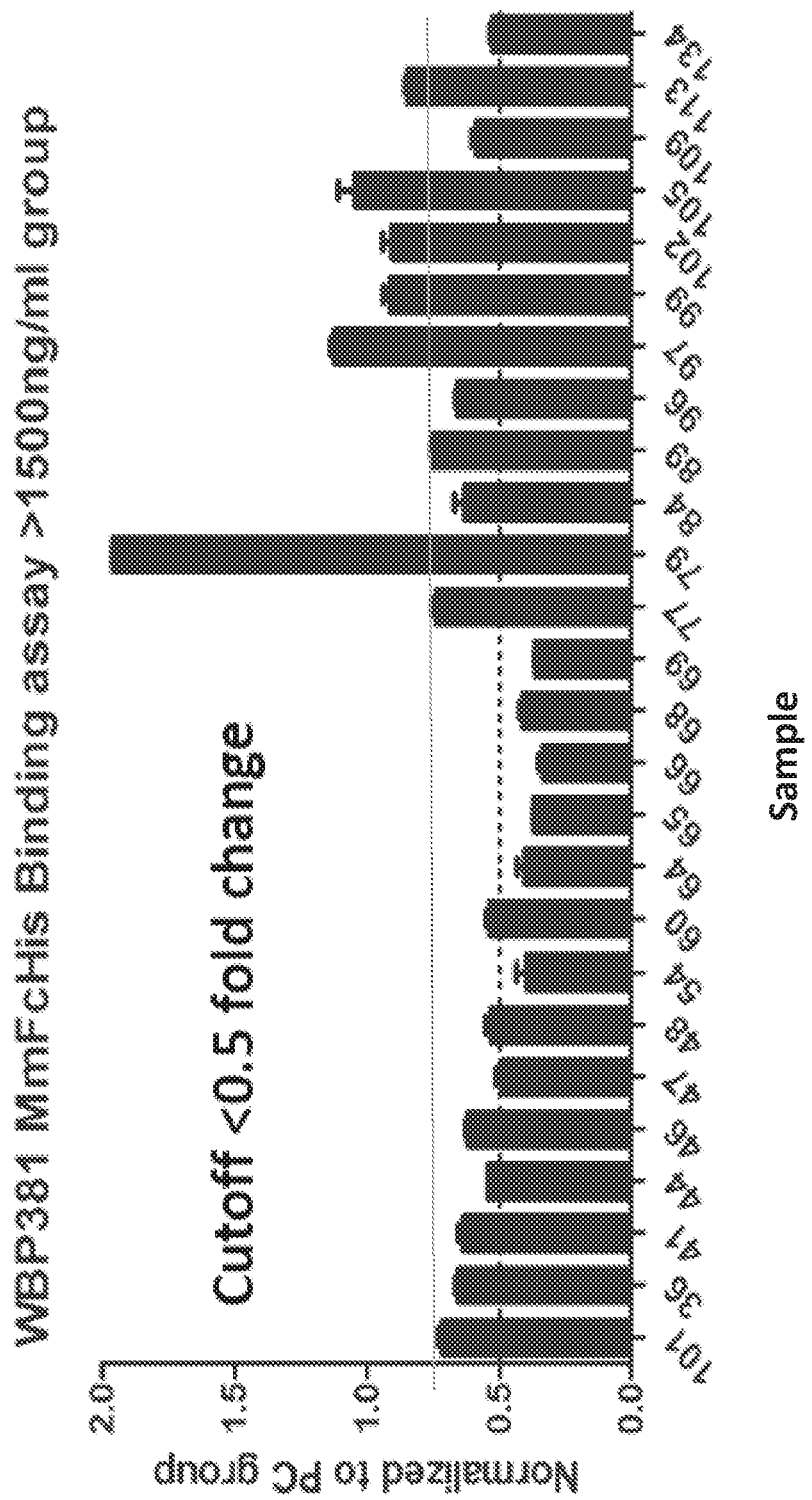
FIG. 6 is a graph plotting the fold change in binding of various TNFRSF25 alanine mutants to an anti-TNFRSF25 antibody.
Figure 7:
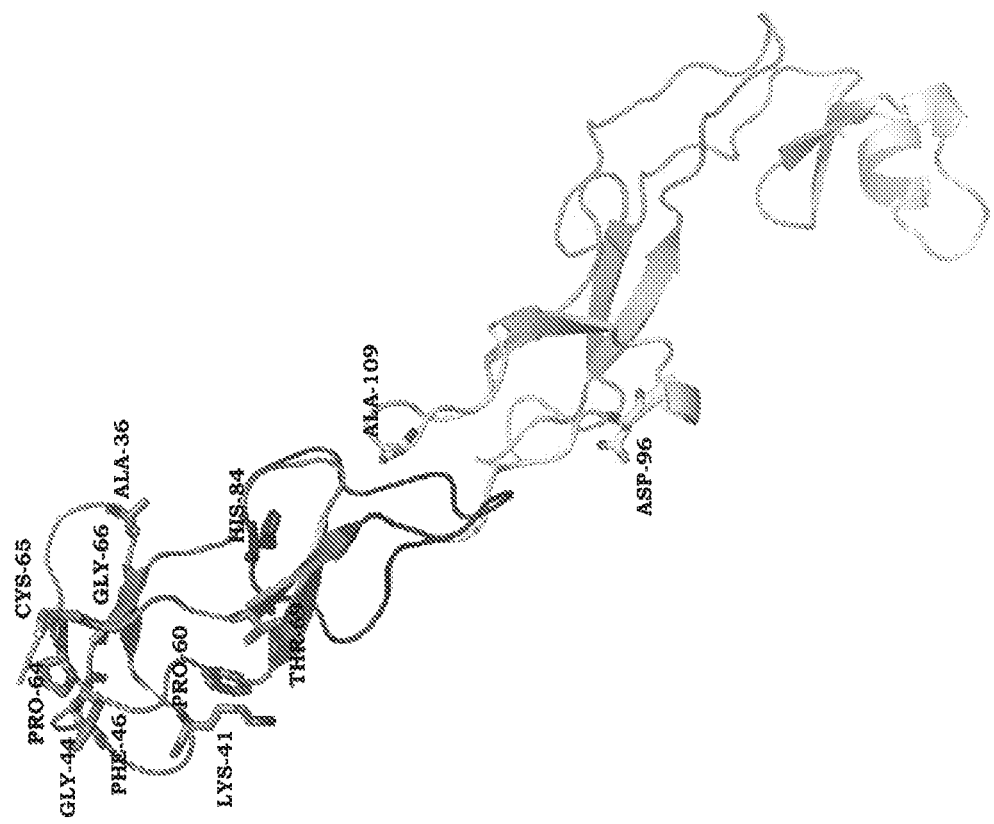
FIG. 7 is a diagram of the structure of TNFRSF25, indicating the positions of residues identified as being involved, or possibly being involved, in antibody binding.
Figure 8:
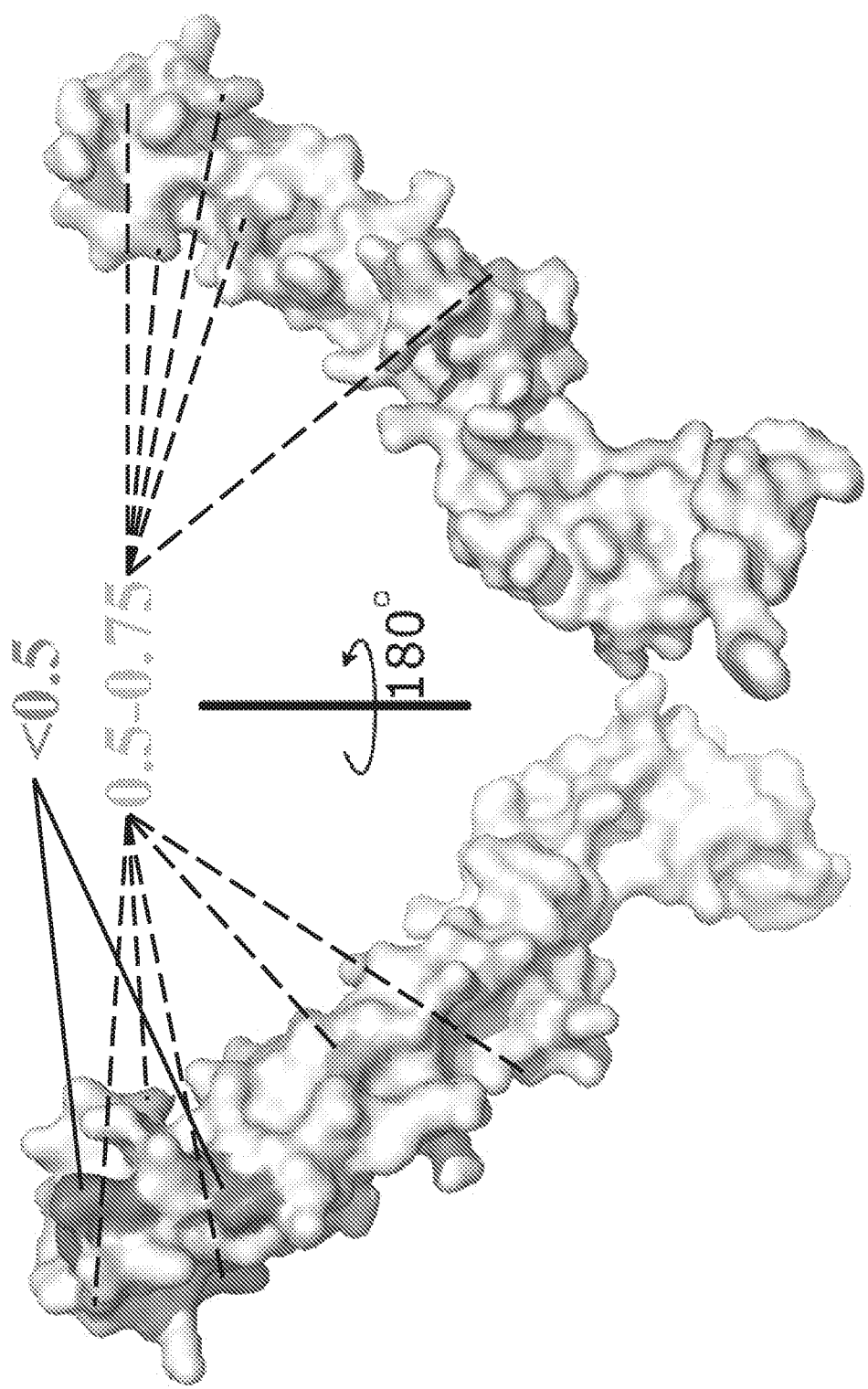
FIG. 8 is a space-filling diagram of the TNFRSF25 structure, viewed from two sides, and indicating the positions of amino acids identified as being involved in antibody binding. "Hot spot" residues were identified as being in the domain between amino acids 48 and 71.

To identify the epitope of TNFRSF25 recognized by the antibody, binding of the antibody to TNFRSF25 muteins was then evaluated using the steps depicted in FIG. 4. Specifically, studies were conducted to assess the binding of a chimeric antibody, W330-cAb1.hIgG1(35783) (the parent, hamster anti-TNFRSF25 antibody that was made chimeric with human IgFc), to alanine mutants of WBP330-hPro1.ECD.hFcHis that were expressed at greater than 1500 ng/ml. The binding affinity to each mutein was compared to that of non-mutated WBP330-hPro1.ECD.hFcHis (FIG. 5). Muteins that exhibited a signal change more than 25% (fold change <0.75; TABLE 3 and FIG. 6) were used for structure modeling (FIGS. 7 and 8).

Figure 9:
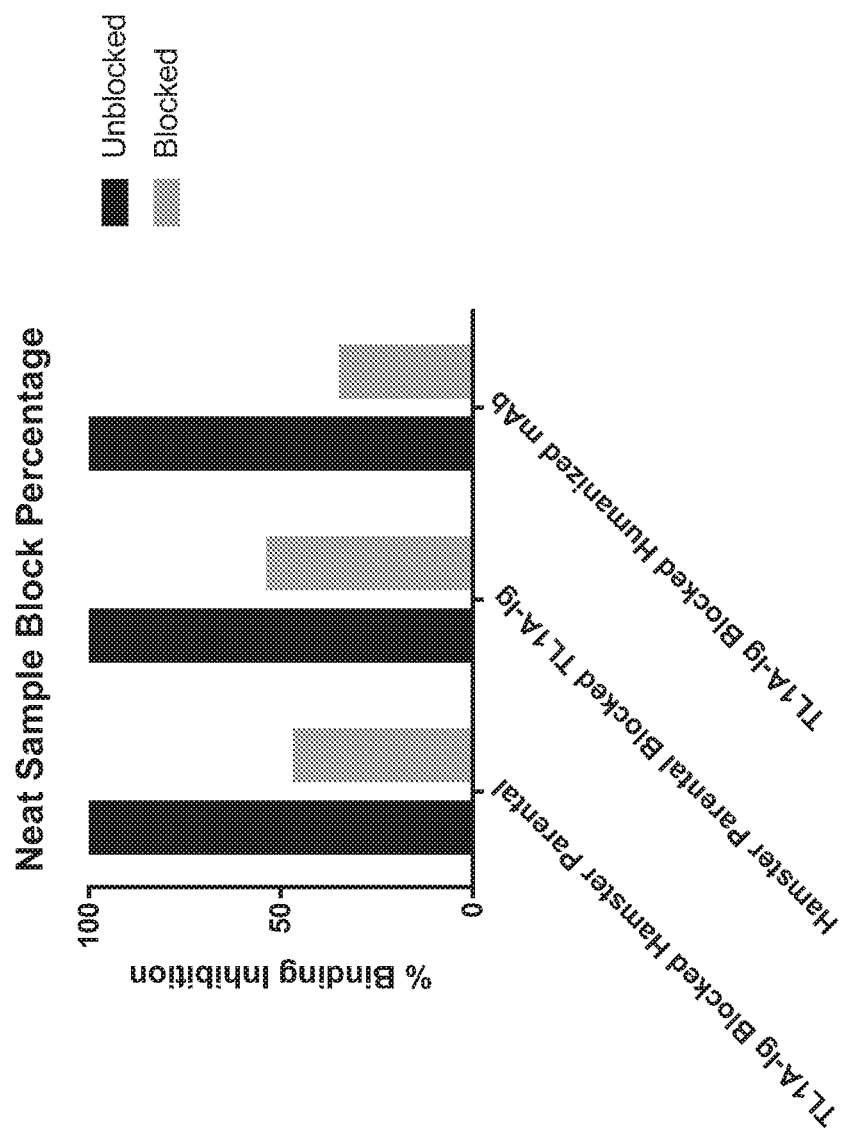
FIG. 9 is a graph plotting inhibition of binding of anti-TNFRSF25 antibodies to TNFRSF25 in the presence or absence of a TL1A-Ig fusion protein, or the inhibition of TL1A-Ig binding to TNFRSF25 in the presence or absence of an anti-TNFRSF25 antibody. Left columns: binding of an anti-TNFRSF25 antibody ("hamster parental") to recombinant human TNFRSF25 was completely inhibited in the presence of TL1A-Ig. Center columns: binding of the TL1A-Ig fusion to recombinant human TNFRSF25 was completely inhibited in the presence of the parental anti-TNFRSF25 antibody. Right columns: binding of a humanized anti-TNFRSF25 antibody to recombinant human TNFRSF25 was completely inhibited in the presence of TL1A-Ig.

In addition, studies were conducted to determine whether the antibody could inhibit binding of TL1A to TNFRSF25, and vice versa. As shown in FIG. 9, the binding of an anti-TNFRSF25 antibody ("hamster parental") to recombinant human TNFRSF25 was blocked by TL1A-Ig (left pair of bars). Conversely, binding of the TL1A-Ig fusion to recombinant human TNFRSF25 was blocked by the parental anti-TNFRSF25 antibody (center pair of bars). In addition, the binding of a humanized anti-TNFRSF25 antibody (derived from the "hamster parental" antibody) to recombinant human TNFRSF25 was blocked by TL1A-Ig (right pair of bars).

hybridization mutagenesis method (Kunkel, *Proc Natl Acad Sci USA* 82(2):488-492, 1985). DNA primers containing a NNS codon encoding 20 amino acids were used to introduce mutations at each targeted CDR position. The individual degenerate primers were used in hybridization mutagenesis reactions. Briefly, each degenerate primer was phosphorylated, then used in a 10:1 ratio with uridinylated ssDNA. The mixture was heated to 85° C. for 5 minutes and then cooled down to 55° C. over 1 hour. Thereafter, T4 ligase and T4 DNA polymerase were added, and mix was incubated for 1.5 hours at 37° C. Synthesis products for VH and VL CDRs were pooled, respectively. Typically, 200 ng of the pooled library DNA was electroporated into BL21 for plaque formation on a BL21 bacterial lawn or for production of scFv fragments.

TABLE 2B

| AA# | ng/ml | AA# | ng/ml | AA# | ng/ml | AA# | ng/ml | AA# | ng/ml |
|---|---|---|---|---|---|---|---|---|---|
| 99 | 2770.3 | 74 | 1483 | 63 | 937.7 | 33 | 566.9 | 154 | 189 |
| 41 | 2759.8 | 58 | 1407.6 | 51 | 878.1 | 121 | 561.8 | NC | 189.4 |
| 64 | 2617.6 | 78 | 1369.9 | 55 | 861.2 | 91 | 520 | | |
| 60 | 2576.9 | 67 | 1360 | 73 | 845.5 | 140 | 482.6 | | |
| 47 | 2515.3 | 34 | 1315.4 | 136 | 825.2 | 123 | 478.8 | | |
| 84 | 2513.1 | 112 | 1255.8 | 133 | 824.7 | 32 | 477.5 | | |
| 54 | 2431.3 | 61 | 1176.1 | 108 | 765.3 | 95 | 474.6 | | |
| 97 | 2401.9 | 92 | 1166.2 | 104 | 735 | 117 | 473.7 | | |
| 65 | 2289.6 | 70 | 1138.2 | 138 | 709.9 | 116 | 470.7 | | |
| 89 | 2230.1 | 49 | 1133.5 | 35 | 693.9 | 130 | 463.1 | | |
| 36 | 2215.5 | 76 | 1062.6 | 107 | 688.1 | 148 | 456.9 | | |
| 59 | 2195.3 | 56 | 1033.5 | 50 | 686.3 | 106 | 373.7 | | |
| 69 | 2158.1 | 52 | 1028.1 | 120 | 671 | 141 | 370.4 | | |
| 77 | 2143.1 | 71 | 1024.9 | 93 | 668.9 | 135 | 326.8 | | |
| 44 | 2082.3 | | | 115 | 649.9 | | | | |
| 101 | 2080.7 | | | 125 | 629.3 | | | | |
| 102 | 2017 | | | 83 | 608.1 | | | | |
| 109 | 1811.1 | | | | | | | | |
| 46 | 1809.2 | | | | | | | | |
| 96 | 1796.5 | | | | | | | | |
| 79 | 1788.2 | | | | | | | | |
| 113 | 1739.1 | | | | | | | | |
| 105 | 1672.4 | | | | | | | | |
| 66 | 1661.7 | | | | | | | | |
| 68 | 1643.4 | | | | | | | | |
| 48 | 1622.4 | | | | | | | | |
| 134 | 1562.6 | | | | | | | | |

NC = Negative control (293F cells only)

TABLE 3

| | Fold change |
|---|---|
| Identified epitope | |
| G66 | 0.33 |
| T69 | 0.37 |
| C65 | 0.37 |
| P64 | 0.40 |
| Possible epitope | |
| P60 | 0.54 |
| G44 | 0.54 |
| A109 | 0.59 |
| F46 | 0.62 |
| H84 | 0.63 |
| K41 | 0.63 |
| A36 | 0.65 |
| D96 | 0.66 |

Example 2—Affinity Maturation and Characterization Methods

Affinity Optimization of W3153-P8R32-H6 Antibody:

Each amino acid of the three CDRs of the parental clone was individually mutated to all 20 amino acids using a The sequences of the parental heavy and light chains, and their CDR and FW regions, were as follows:

```
Heavy chain variable region:
                                         (SEQ ID NO: 5)
EVQLVESGGGLSQPGNSLQLSCEASGFTFSNH
DLNWVRQAPGKGLEWVAYISSASGLISYADAVRGRFTISRDNAKNSLFLQ
MNNLKSEDTAMYYCARDPPYSGLYALDFWGQGTQVTVSS FW1:
                                         (SEQ ID NO: 11)
EVQLVESGGGLSQPGNSLQLSCEAS

CDR1:
                                         (SEQ ID NO: 12)
GFTFSNHDLN

FW2:
                                         (SEQ ID NO: 13)
WVRQAPGKGLEWVA

CDR2:
                                         (SEQ ID NO: 14)
YISSASGLISYADAVRG
```

-continued

FW3:
(SEQ ID NO: 15)
RFTISRDNAKNSLFLQMNNLKSEDTAMYYCAR

CDR3:
(SEQ ID NO: 6)
DPPYSGLYALDF

FW4:
(SEQ ID NO: 17)
WGQGTQVTVSS

Light chain variable region:
(SEQ ID NO: 6)
QPVLTQSPSASASLSGSVKLTCTLSSELSSYT
IVWYQQRPDKAPKYVMYLKSDGSHSKGDGIPDRFSGSSSGAHRYLSISNV
QSEDDATYFCGAGYTLAGQYGWVFGSGTKVTVL

FW1:
(SEQ ID NO: 18)
QPVLTQSPSASASLSGSVKLTC

CDR1:
(SEQ ID NO: 19)
TLSSELSSYTIV

FW2:
(SEQ ID NO: 20)
WYQQRPDKAPKYVMY

CDR2:
(SEQ ID NO: 21)
LKSDGSHSKGD

FW3:
(SEQ ID NO: 22)
GIPDRFSGSSSGAHRYLSISNVQSEDDATYF

CDR3:
(SEQ ID NO: 23)
CGAGYTLAGQYGWV

FW4:
(SEQ ID NO: 24)
FGSGTKVTVL

Primary Screening of the scFv Library:

The primary screen consisted of a single point ELISA (SPE) assay, which was carried out using periplasmic extract (PE) of bacteria grown in 96-well (deep well) plates. Briefly, this capture ELISA involved coating individual wells of a 96-well Maxisorp Immunoplate with anti-c-myc antibody in coating buffer (200 mM $Na_2CO_3/NaHCO_3$) at pH 9.2 overnight at 4° C. The next day, the plate was blocked with Casein for 1 hour at room temperature. scFv PE was then added to the plate and incubated at room temperature for 1 hour. After washing, biotinylated antigen protein was added to the well and the mixture was incubated for 1 hour at room temperature. This was followed by incubation with streptavidin-horseradish peroxidase (HRP) conjugate for 1 hour at room temperature. HRP activity was detected with tetramethyl-benzidine (TMB) substrate, and the reaction was quenched with 2M HCl. Plates were read at 450 nM. Clones exhibiting an optical density (OD) signal at 450 nm that was greater than the OD signal of the parental clone were picked and re-assayed by ELISA (as described above) in duplicate, to confirm positive results. Clones that repeatedly exhibited a signal greater than that of the parental antibody were sequenced. The scFv protein concentration of each clone that had a CDR change was then determined by a quantitative scFv ELISA, where a scFv with known concentration was used as a reference. The scFv protein concentration was determined by comparing the ELISA signals with signals generated by the reference scFv. The binding assay was repeated once more for all positive variants under normalized scFv concentrations in order to determine the relative binding affinity of the mutant scFv and the parental antibody.

Selected scFv hits displaying improved binding were re-formulated to IgG1 and tested in a caspase-3 assay as described below.

Combinatorial Screening of the scFv Library:

Point mutations in the VH and VL chains that were determined to be beneficial for binding to antigen were combined to determine whether additional binding synergy was attained. The combinatorial mutants were expressed as scFv and screened using the capture ELISA. Clones exhibiting an OD signal at 450 nm that was greater than the OD signal of the parental clone were sequenced and further ranked by binding ELISA as described above. Eleven top-ranked clones were selected for IgG4 re-formatting and further characterization as described above.

Reformatting, Transient Expression, and Purification of 4C12 Mutants with Improved Affinity:

V-genes of the top-rScFv clones identified from the primary and combinatorial screening were amplified by PCR and cloned into WuXi Biologics' proprietary expression vector, and expressed from 293F cells. Culture supernatants containing the antibodies were harvested and purified using Protein A chromatography.

Caspase Release Assay:

P815 cells expressing TNFRSF25 were incubated with various concentrations of antibodies (from 1 µg/ml to 1 ng/ml) for 5 hours at 37° C. in a 96-well plate. Caspase activity was determined using the Homogeneous Caspase Assay kit (Roche: 005372001). Fluorescence was read using a Molecular Devices SPECTRAIVIAX® M5e plate reader.

Competition Assays:

Parental p815 cells and p815 cells expressing human TNFRSF25 (also referred to as p815-hDR3) were cultured in suspension in IMDM+10% FBS. Cells were counted at the time of harvest, pelleted and resuspended at a concentration of 300,000 cells/100 µL in serum free media. 100 µL aliquots of the cell suspension were placed into Eppendorf tubes.

ALEXA FLUOR® 647 (AF647)-conjugated 4C12 and hTL1A-Ig (AKTA purification, round 1) were generated using a Molecular Probes ALEXA FLUOR® labeling kit (RL#170512) per the manufacturer's instructions. The degree of labeling for 4C12-AF647 was 5.98 moles of dye to antibody, and for hTL1A-Ig-AF647 the degree of labeling was 4.55 moles of dye to protein (both considered to be within the acceptable range).

hTL1A-Ig-AF647 or 4C12-AF647 was added to the Eppendorf tubes at a concentration of 0.5 µg/mL. Unlabeled 4C12, affinity matured 4C12 (hIgG1 subtype), or isotype control hIgG1 was added immediately afterward at concentrations ranging from 2 µg/mL to 0.0078 µg/mL. The mixtures were as incubated at 37° C. in a humidified incubator with 5% $CO_2$ for 1 hour. Cells were pelleted in a microcentrifuge and washed 1× with FACS buffer. Pellets were resuspended in 300 µL FACS buffer and analyzed by a Sony SH800 flow cytometer. Live single cells were gated on, and MFI for AF647 was determined for each sample.

Example 3—Affinity Maturation and Characterization Results

Primary screening yielded 11 mutants at 7 CDR positions that showed capture ELISA signal at least 2-fold higher than that of the wild-type (TABLE 4). Multiple mutations at position 42 in the light chain CDR1 consistently showed improved binding to TNFRSF25-Fc protein. Substitution of Ser to Trp at this position resulted in more than a 10-fold increase in ELISA signal. Two other mutations, Ala to Thr at position 27 in the heavy chain CDR3 and Tyr to Phe at position 43 in the light chain CDR1 also showed significant binding improvement. These mutants were converted to IgG1 and tested for activity using a caspase-3 assay (TABLE 5). Only the mutants at position 42 showed improved potency in the caspase-3 release assay. One particular IgG clone, W3072-z4C12-R1-42G2-uIgG1L, which contains the Ser to Trp mutation in the light chain CDR1, showed the highest increase in caspase-3 agonistic activity.

TABLE 4

Primary screening hits

| CDR | Sample ID | OD$_{450}$ | Mutation | WT* OD$_{450}$ | BMK¶ OD$_{450}$ | NC† OD$_{450}$ | PC‡ OD$_{450}$ |
|---|---|---|---|---|---|---|---|
| VHCDR2 | 10C3 | 0.70 | A→D | 0.28 | 0.13 | 0.12 | 0.35 |
| VHDCR2 | 12F7 | 0.85 | G→Q | 0.26 | 0.10 | 0.10 | 0.41 |
| VHCDR3 | 27A3 | 1.61 | S→T | 0.29 | 0.12 | 0.08 | 0.53 |
| VLCDR1 | 42F2 | 0.83 | S→G | 0.27 | 0.13 | 0.09 | 0.34 |
|  | 42G2 | 3.19 | S→W | 0.27 | 0.13 | 0.09 | 0.34 |
|  | 42H4 | 1.21 | S→N | 0.27 | 0.13 | 0.09 | 0.34 |
|  | 42H8 | 1.67 | S→Y | 0.27 | 0.13 | 0.09 | 0.34 |
|  | 42F9 | 2.33 | S→F | 0.27 | 0.13 | 0.09 | 0.34 |
|  | 43F11 | 1.60 | Y→F | 0.22 | 0.10 | 0.09 | 0.45 |
| VHCDR3 | 60E8 | 0.44 | A→M | 0.11 | 0.07 | 0.05 | 0.16 |
| VHCDR3 | 66B8 | 0.40 | G→N | 0.15 | 0.07 | 0.06 | 0.20 |

*W3072-z4C12-scFv
¶W381-1H11-scFv
†Non-specific control
‡W3072-z4C12 parental clone

TABLE 5

Caspase Release Results

| Ab | EC50 |
|---|---|
| W3072-z4C12-R1-60H10-uIgG1L | 0.085 |
| W3072-z4C12-R1-66B8-uIgG1L | 0.071 |
| W330-cAb1.hIgG1 (35783) | 0.065 |
| W330-hpro1L1 (TL1A) | ~0.334 |
| W330-hAb.35816 | 0.115 |
| W3343-P6R31-1B2-uIgG1L | 1.771 |
| W3072-z4C12-R1-27A4-uIgG1L | 0.142 |
| W3072-z4C12-R1-42F2-uIgG1L | 0.057 |
| W3072-z4C12-R1-42G2-uIgG1L | 0.018 |
| W3072-z4C12-R1-42H8-uIgG1L | 0.032 |

TABLE 5-continued

Caspase Release Results

| Ab | EC50 |
|---|---|
| W3072-z4C12-R1-42F9-uIgG1L | 0.043 |
| W3072-z4C12-R1-43F11-uIgG1L | ~0.1 |

Figure 10:
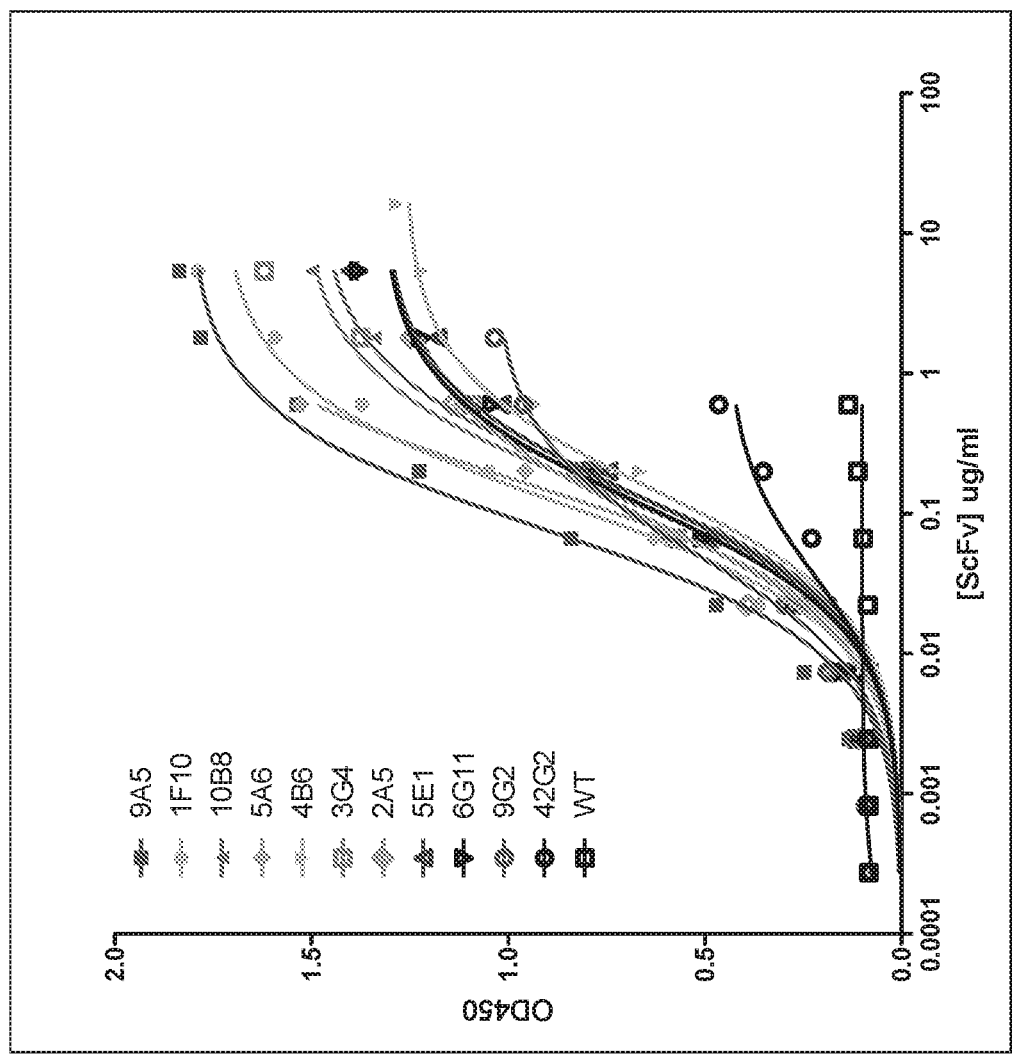
FIG. 10 is a graph plotting the binding of parent humanized anti-TNFRSF25 antibody and affinity matured clones to a TNFRSF25-Fc fusion protein.

All individual affinity-improving mutations identified in the primary screening were used to design and construct a combinatorial mutant library. This library was screened to identify combinations of mutations that had synergistic effects on binding improvement. Single mutant clone 42G2 was used as the benchmark. Multiple combination mutant clones with significantly improved binding to TNFRSF25-Fc protein were identified (FIG. 10). However, only one combination mutant, 9G2, included the Ser to Trp mutation in the light chain CDR1. This clone, as well as three additional clones that displayed the strongest binding to TNFRSF25-Fc protein (9A5, 1F10, and 5A6) were selected for IgG conversion and further testing (TABLE 6).

TABLE 6

| Well Site | VHCDR3 | (SEQ ID) | VLCDR1 | (SEQ ID) | VLCDR3 | (SEQ ID) | Bmax | Kd |
|---|---|---|---|---|---|---|---|---|
| z4C12 | DPPYSGLYALDF | (16) | TLSSELSSYTIV | (19) | CGAGYTLAGQYGWV | (23) | 0.1002 | 0.00008994 |
| 42G2 | ............ | (16) | .......W.... | (25) | .............. | (23) | 0.4468 | 0.03675 |
| 9A5 | ..A.T....... | (26) | .......GF... | (27) | ........N..... | (28) | 1.811 | 0.07688 |
| 1F10 | ..A.T....... | (26) | .......NF... | (29) | ........S..... | (30) | 1.731 | 0.1177 |
| 10B8 | ..A......... | (31) | .......NF... | (29) | .............. | (23) | 1.486 | 0.1621 |
| 5A6 | ....T....... | (32) | .......NF... | (29) | ........N..... | (28) | 1.887 | 0.1602 |
| 4B6 | ..A.T....... | (26) | .......N.... | (33) | ........N..... | (28) | 1.263 | 0.1488 |
| 3G4 | ..A.T....... | (26) | .......GF... | (27) | ........R..... | (34) | 1.527 | 0.1464 |
| 2A5 | ..A.T....... | (26) | .......NF... | (29) | ..M.....N..... | (35) | 1.282 | 0.09108 |
| 5E1 | ..A.T....... | (26) | .......N.... | (33) | ..M.....N..... | (35) | 1.322 | 0.1303 |
| 6G11 | ............ | (16) | .......NF... | (29) | .............. | (23) | 1.325 | 0.1172 |
| 9G2 | ..A.T....... | (26) | .......W.... | (25) | .............. | (23) | 1.038 | 0.05068 |

After IgG conversion, clones with improved binding to the TNFRSF25-Fc protein were designated as follows:

1F10→W3072-z4C12-m1 (also referred to herein as M1)
5A6→W3072-z4C12-m2 (also referred to herein as M2)
9A5→W3072-z4C12-m3 (also referred to herein as M3)
9G2→W3072-z4C12-m4 (also referred to herein as M4)
42G2→W3072-z4C12-m5 (also referred to herein as M5)

Figure 11A:
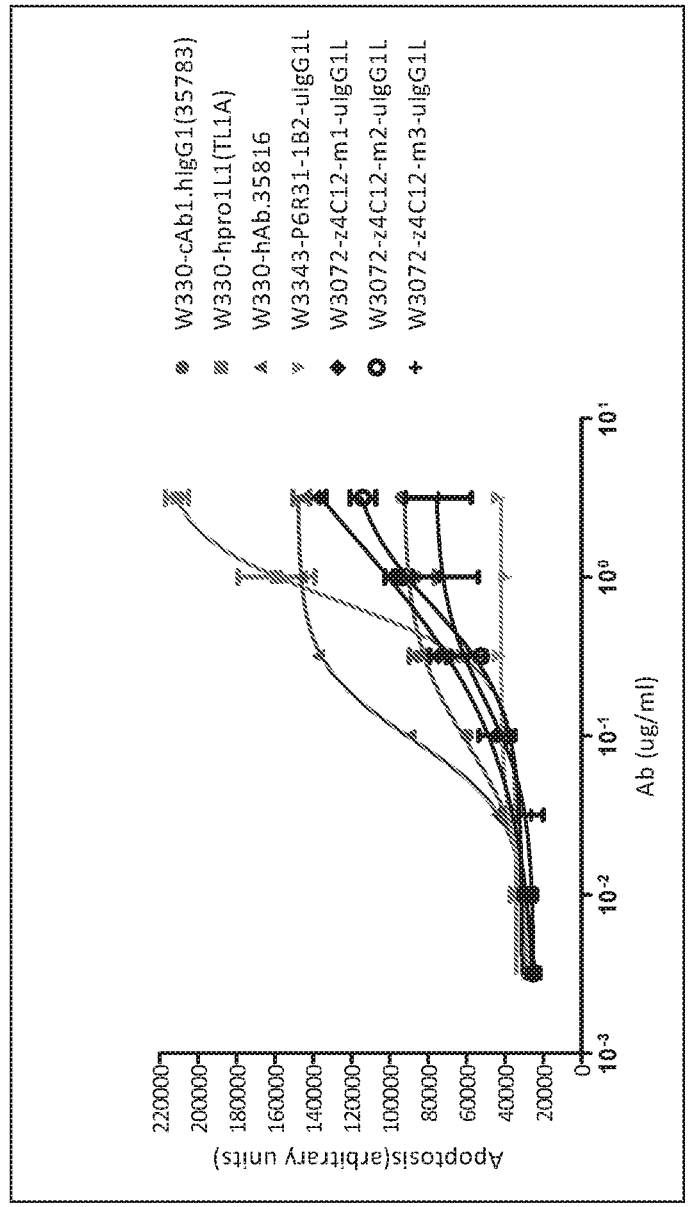
FIGS. 11A and 11B are graphs plotting caspase activity of parent anti-TNFRSF25 antibody, TL1A, and the indicated affinity matured clones. The affinity matured clones were in an IgG1 format.
Figure 11B:
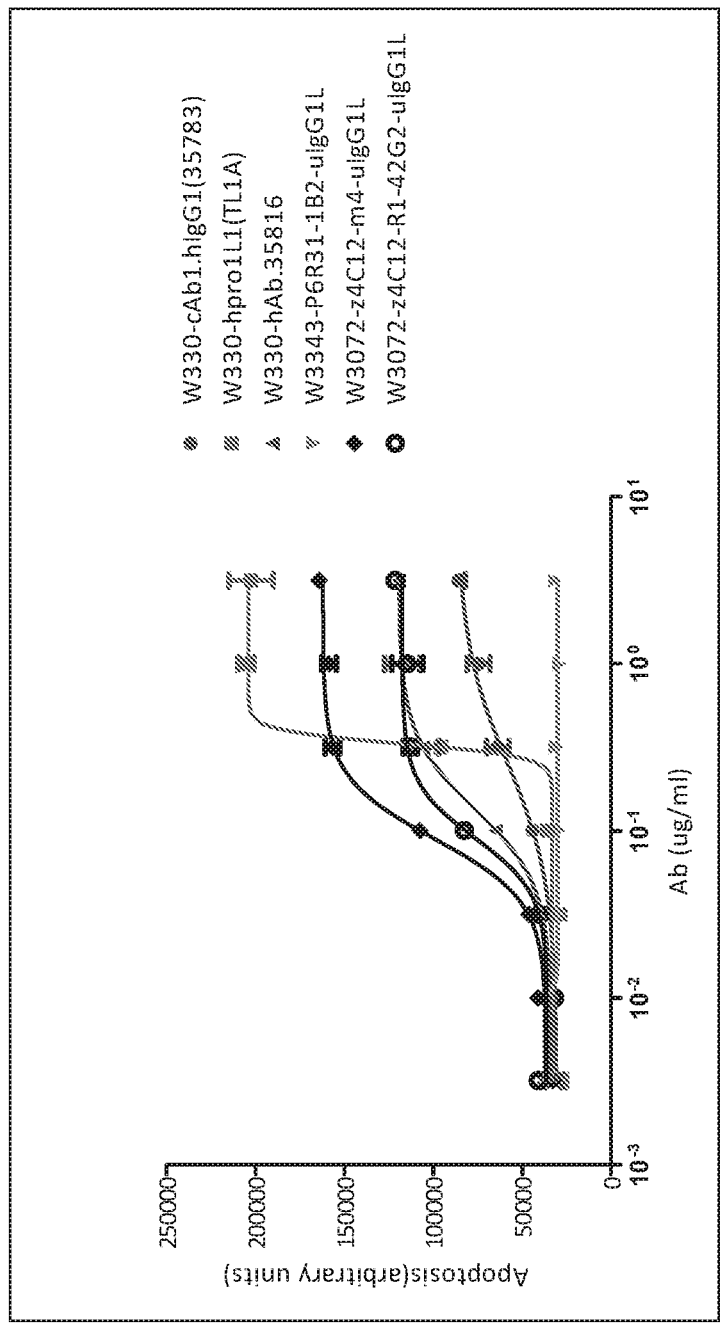
Figure 12:
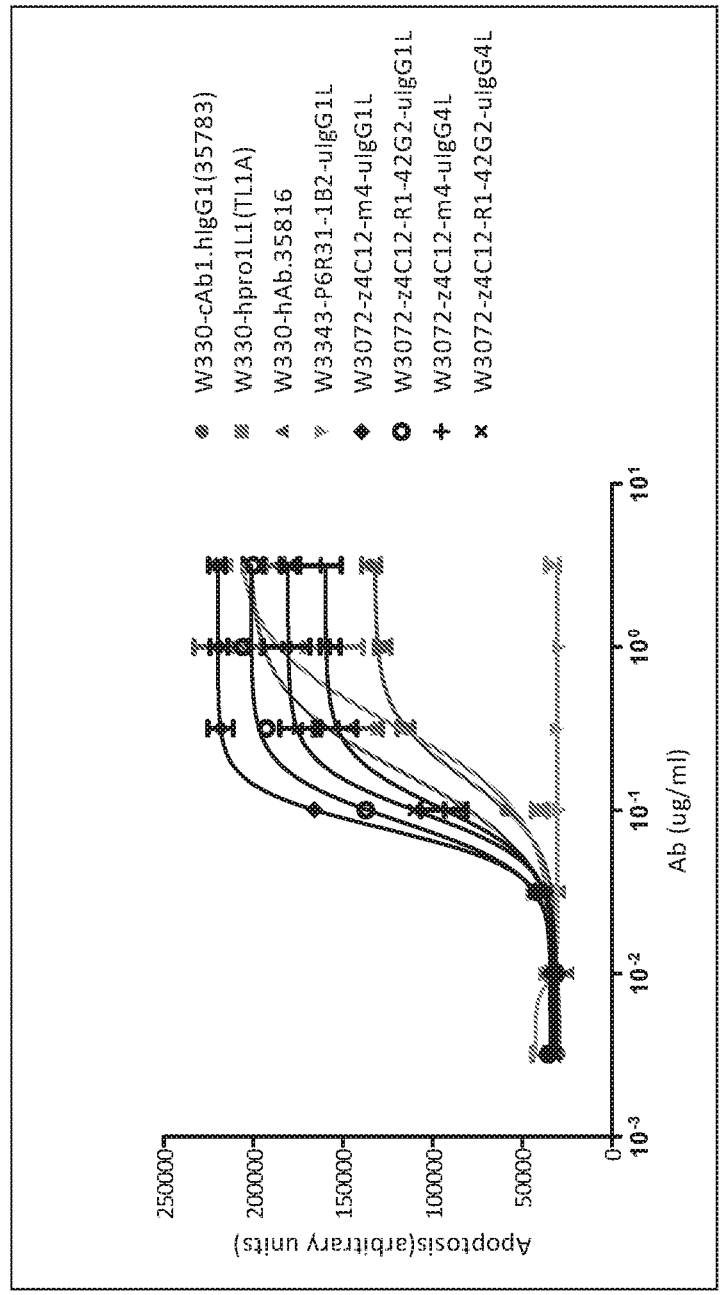
FIG. 12 is a graph plotting caspase activity of parent anti-TNFRSF25 antibody, TL1A, and the indicated affinity matured clones. The affinity matured clones were in an IgG1 or IgG4 format, as indicated.

Caspase-3 release assays revealed that only M5 and M4 (both containing the Ser→Trp substitution in the light chain CDR1) showed improved agonistic activity as compared to the parental humanized clone (W330-hAb35816, generated by CDR grafting) and the natural ligand TL1A, while three other mutants showed inferior agonistic activity (FIGS. 11A and 11B, TABLE 6) but higher affinity binding to TNFRSF25 than the parent antibody (FIG. 10). Interestingly, the M4 higher affinity clone had a higher amplitude of response than the M5 clone (FIG. 11B). The highest affinity clone, M3, had agonist activity that was inferior to that of the parental humanized antibody and the chimeric clone (FIG. 11A). It also was surprising that humanized parent had a markedly superior amplitude of response as compared to the chimeric parent antibody (FIG. 11A).

M5 and M4 were reformatted to IgG4, and the IgG1 and IgG4 formats were both tested in the caspase-3 release assay. These studies revealed that the IgG1 formatted antibodies consistently showing improved agonistic activity as compared to the parental humanized 4C12 IgG1 (W330-hAb35816; TABLE 7).

TABLE 7

| Ab | EC50 |
| --- | --- |
| W330-cAb1.hIgG1 (35783) | 0.088 |
| W330-hproL1 (TL1A) | 0.706 |
| W330-hAb.35816 | 0.095 |
| W3343-P6R31-1B2-uIgG1L | NA |
| M1-uIgG1L | 1.839 |
| M2-uIgG1L | 0.656 |
| M3-uIgG1L | 0.17 |
| M4-uIgG1L | 0.07 |
| M5-uIgG1L | 0.08 |
| M4-uIgG4L | 0.1 |
| M5-uIgG4L | 0.1 |

Figure 13A:
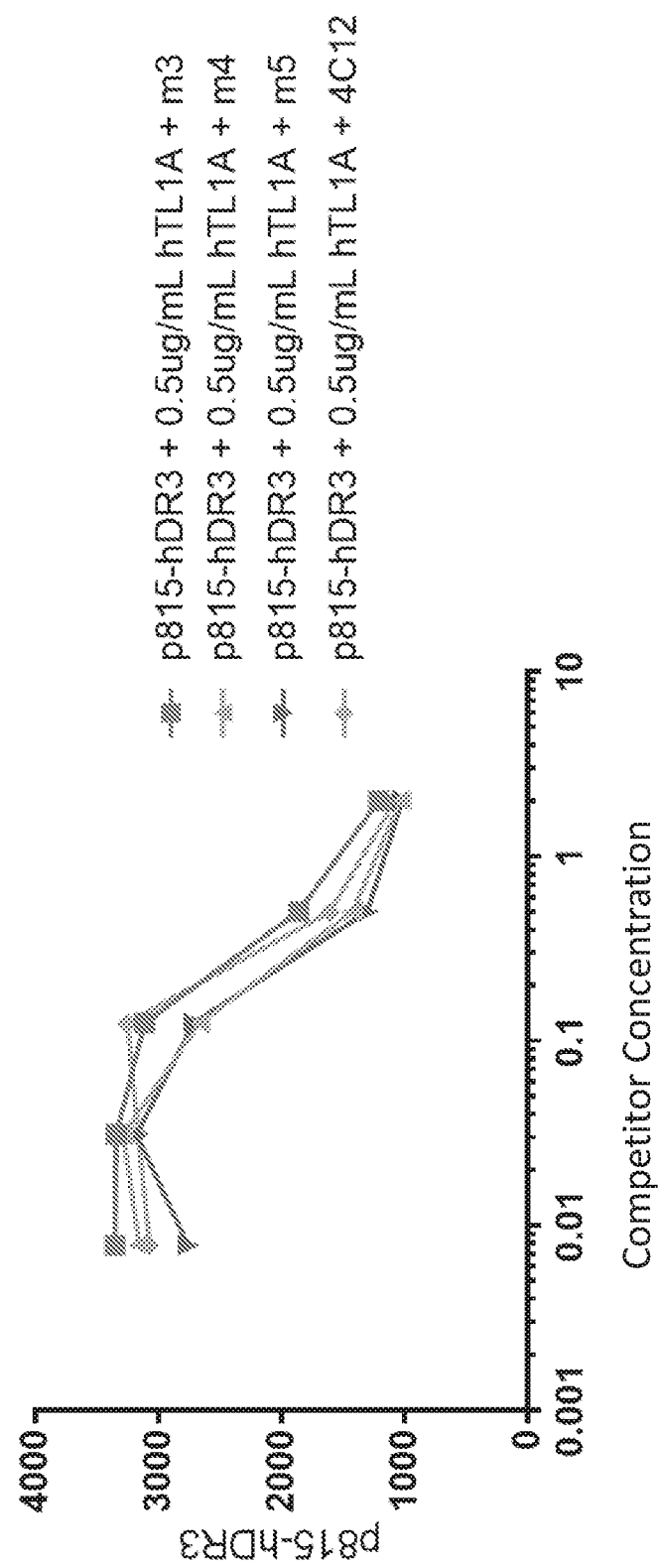
FIG. 13A is a graph plotting fluorescence levels in competition assays in which ALEXAFLUOR® 647-labeled TL1A and various antibody competitors (4C12 parent and the M3, M4, and M5 affinity matured clones) were incubated with p815 cells expressing TNFRSF25 (DR3).

Competition studies were conducted to determine whether the affinity matured antibodies could compete with 4C12 or TL1A for binding to TNFRSF25. In a first experiment, all samples received 0.5 µg/mL hTL1A-Ig-AF647, which was competed off with unlabeled 4C12-M3, 4C12-M4, 4C12-M5, and 4C12. As indicated in FIG. 13A, the M4 and M5 antibodies demonstrated stronger competition against TL1A than the 4C12 parent antibody. Thus, although M4 and M5 showed weaker binding to TNFRSF25-Fc than M3 (9A5; FIG. 10) but stronger binding than the parent antibody (WT; FIG. 10), they appeared to be stronger competitors of TL1A binding to cell surface-expressed TNFRSF25. Samples receiving no hTL1A-Ig-AF647 had a MFI of about 1000, and samples receiving hIgG1 isotype had an MFI of about 3320.

Figure 13B:
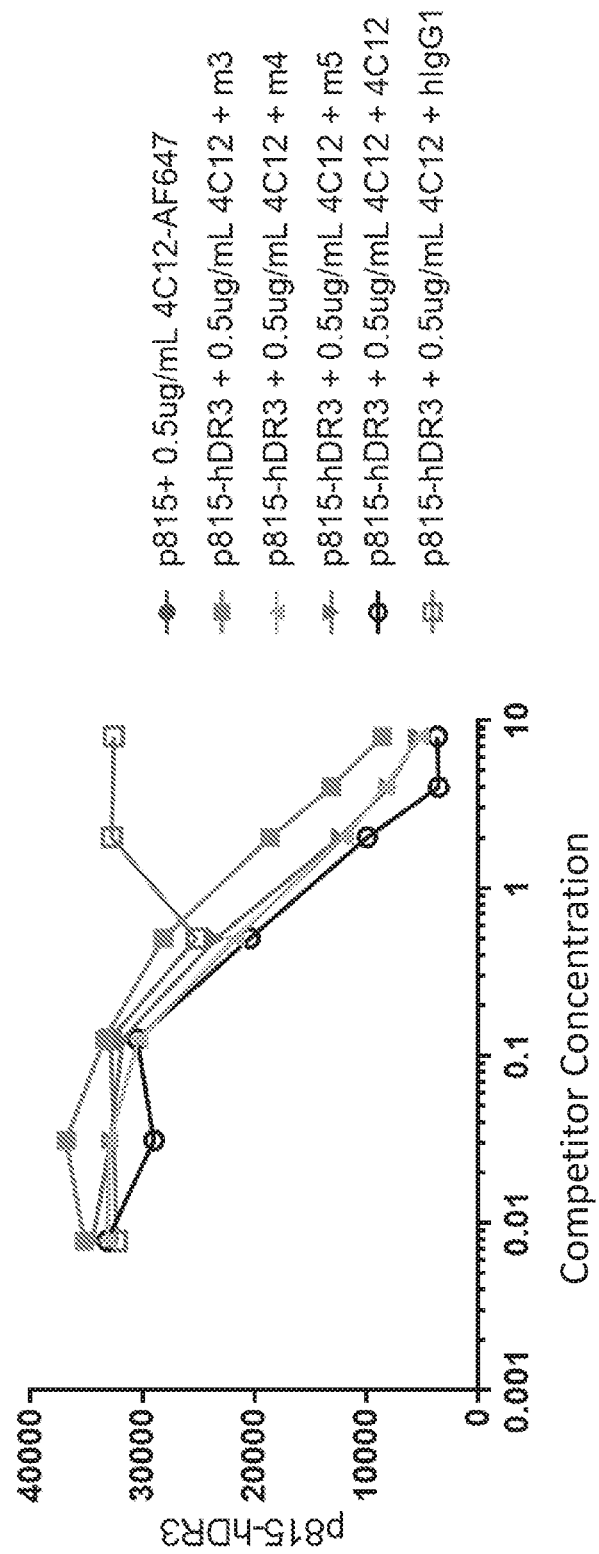
FIG. 13B is a graph plotting fluorescence levels in competition assays in which ALEXAFLUOR® 647-labeled 4C12 and various antibody competitors (4C12 parent, hIgG1, and the M3, M4, and M5 affinity matured clones) were incubated with p815 cells expressing TNFRSF25 (DR3).

Further competition assays were conducted in which all samples received 0.5 µg/mL 4C12-AF647, which was competed off with unlabeled 4C12-M3, 4C12-M4, and 4C12-M5 at extended unlabeled antibody concentrations up to 8 µg/mL to complete the binding curve. As indicated in FIG. 13B, unlabeled 4C12 parent competed off labeled 4C12, while isotype hIgG1 had no competitive effect. Samples receiving no 4C12-AF647 had an MFI of about 1400. The 4C12, M4, and M5 affinity matured antibodies demonstrated similar competition against labeled 4C12, while M3 was the weakest competitive inhibitor.

Thus, when humanized 4C12 antibody was affinity matured, primary screening (by saturated mutagenesis of antibody CDRs) identified multiple mutants with improved binding to TNFRSF25-Fc protein. In particular, clone M5 containing a Ser→Trp mutation in the light chain CDR1 showed improved agonistic activity as determined by caspase-3 release assay. Combinatorial library screening yielded multiple mutants with significantly stronger binding than M5 to a TNFRSF25-Fc protein, but surprisingly, most of these displayed inferior agonistic activity as compared to the parental antibody. The exception to this was M4, which contained the same Ser→Trp mutation in the light chain CDR1 as M5. Only M5 and M4 showed both improved agonistic activity in the caspase-3 release assay and improved binding to the TNFRSF25-Fc fusion protein. In addition, these clones also displayed stronger competition binding against TL1A to cellularly-expressed TNFRSF25 as compared to the 4C12 parent (FIG. 13A) while maintaining comparable competition against 4C12 binding to TNFRSF25 (FIG. 13B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An anti-tumor necrosis factor superfamily receptor 25 (TNFRSF25) antibody, comprising:
   (a) a heavy chain, said heavy chain comprising:
      (i) a heavy chain variable region comprising CDR1, CDR2, and CDR3 sequences, wherein the CDR1 sequence is GFTFSNHDLN (SEQ ID NO: 12), the CDR2 sequence is YISSASGLISYADAVRG (SEQ ID NO: 14); and the CDR3 sequence is DPAYTGLYALDF (SEQ ID NO: 26) or DPPYSGLYALDF (SEQ ID NO: 16); and
   (b) a light chain, said light chain comprising:
      (ii) a light chain variable region comprising CDR1, CDR2, and CDR3 sequences, wherein the CDR1 sequence is TLSSELSWYTIV (SEQ ID NO: 25), the CDR2 sequence is LKSDGSHSKGD (SEQ ID NO: 21), and the CDR3 sequence is CGAGYTLAGQYGWV (SEQ ID NO: 23).

2. The antibody of claim 1, wherein the heavy chain variable region comprises the amino acid sequence of SEQ ID NO: 5.

3. The antibody of claim 1, wherein the light chain variable region comprises the amino acid sequence of SEQ ID NO: 6.

4. The antibody of claim 1, wherein the heavy chain variable region comprises the amino acid sequence of SEQ ID NO: 5 and the light chain variable region comprises the amino acid sequence of SEQ ID NO: 6.

5. The antibody of claim 1, wherein the heavy constant region of said antibody is selected from human IgG1, IgG2, IgG3, and IgG4.

6. The antibody of claim 5, wherein the heavy constant region is from IgG4.

7. A method of treating a tumor in a subject, comprising administering to a subject the antibody of claim 1.

8. A nucleic acid encoding an anti-TNFRSF25 antibody comprising:
   (a) a first nucleic acid sequence encoding a heavy chain polypeptide comprising a heavy chain variable region comprising CDR1, CDR2, and CDR3 sequences, wherein the CDR1 sequence is GFTFSNHDLN (SEQ ID NO: 12), the CDR2 sequence is YISSASGLISYADAVRG (SEQ ID NO: 14); and the CDR3 sequence is DPAYTGLYALDF (SEQ ID NO: 26) or DPPYSGLYALDF (SEQ ID NO: 16); and
   (b) a second nucleic acid sequence encoding a light chain polypeptide comprising a light chain variable region comprising CDR1, CDR2, and CDR3 sequences, wherein the CDR1 sequence is TLSSELSWYTIV (SEQ ID NO: 25), the CDR2 sequence is LKSDGSHSKGD (SEQ ID NO: 21), and the CDR3 sequence is CGAGYTLAGQYGWV (SEQ ID NO: 23).

9. A host cell comprising the nucleic acid of claim 8.

10. A method of making an anti-TNFRSF25 antibody, comprising:
   a) providing the host cell of claim 9;
   b) culturing said host cell under conditions wherein said antibody is expressed, and
   c) recovering said antibody from the host cell.

* * * * *